(12) United States Patent
Fukuda et al.

(10) Patent No.: US 10,174,004 B2
(45) Date of Patent: Jan. 8, 2019

(54) PRODUCTION METHOD OF PYRIDAZINONE COMPOUNDS

(71) Applicant: TAKEDA PHARMACEUTICAL COMPANY LIMITED, Osaka (JP)

(72) Inventors: Naohiro Fukuda, Osaka (JP); Tomomi Ikemoto, Osaka (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/768,784

(22) PCT Filed: Feb. 20, 2014

(86) PCT No.: PCT/JP2014/054780
§ 371 (c)(1),
(2) Date: Aug. 19, 2015

(87) PCT Pub. No.: WO2014/129668
PCT Pub. Date: Aug. 28, 2014

(65) Prior Publication Data
US 2016/0002209 A1   Jan. 7, 2016

(30) Foreign Application Priority Data

Feb. 21, 2013   (JP) ................................ 2013-032326

(51) Int. Cl.
*C07D 403/04* (2006.01)
*C07D 231/12* (2006.01)
*C07D 403/10* (2006.01)

(52) U.S. Cl.
CPC ......... *C07D 403/04* (2013.01); *C07D 231/12* (2013.01); *C07D 403/10* (2013.01)

(58) Field of Classification Search
CPC .................................................. C07D 231/12
See application file for complete search history.

(56) References Cited

U.S. PATENT DOCUMENTS 5,877,175 A    3/1999  Sargent et al.
9,150,588 B2 * 10/2015  Taniguchi ............ C07D 401/04
(Continued)

FOREIGN PATENT DOCUMENTS

WO    96/30364       10/1996
WO    2010/063610    6/2010
(Continued)

OTHER PUBLICATIONS

Salvatore Plescia et al., "Studies on the Synthesis of Heterocyclic Compounds. Part V. A Novel Synthesis of Some Pyridazin-4-(1H)one Derivatives and their Reaction with Hydrazine", Journal of Heterocyclic Chemistry, 18(2), pp. 333-334, Mar. 1981.

(Continued)

*Primary Examiner* — Paul V Ward
(74) *Attorney, Agent, or Firm* — Wenderoth, Lind & Ponack, L.L.P.

(57) ABSTRACT

The present invention provides an industrially advantageous method of producing a pyridazinone compound. The present invention relates to the following method of producing a pyridazinone compound: Formula (II), (IIIa), (IV) or (IV'''), Formula (IIIb), (Vb) or (V''b), Formula (VI), (I) or (I''), wherein each symbol is as described in the specification.

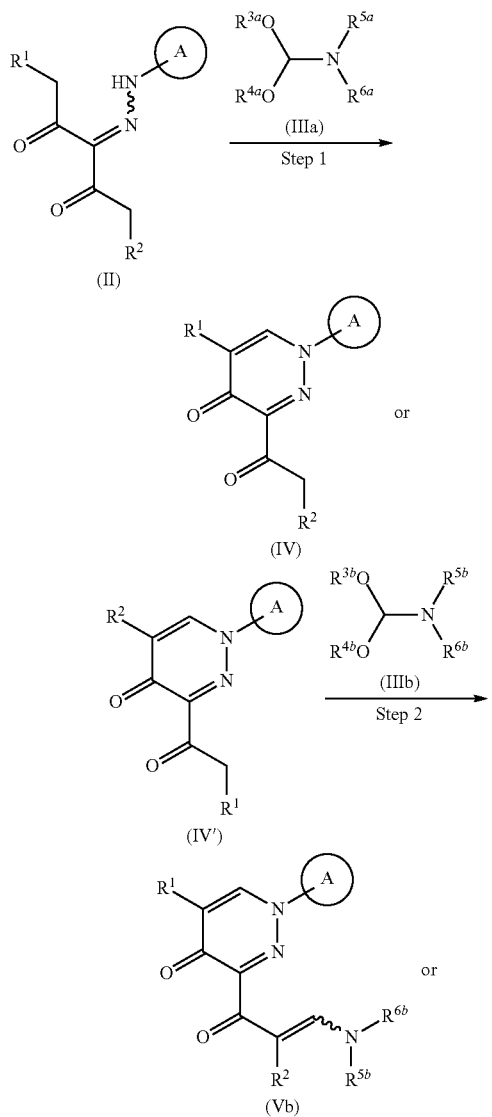

(Continued)

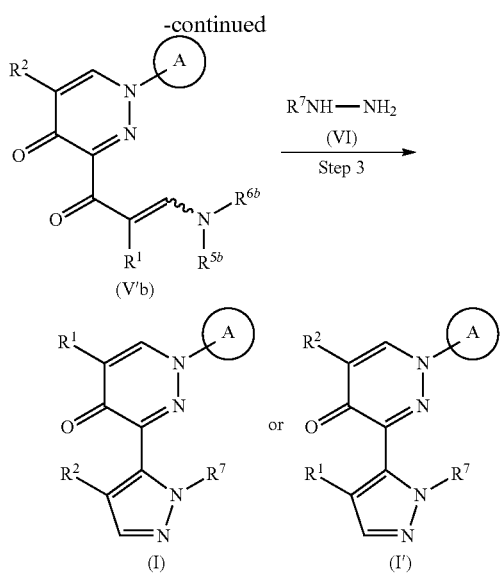

5 Claims, No Drawings

(56) References Cited

U.S. PATENT DOCUMENTS

| | | | |
|---|---|---|---|
| 9,579,407 B2 * | 2/2017 | Taniguchi | C07D 401/14 |
| 2010/0152193 A1 | 6/2010 | Alberati et al. | |
| 2010/0197651 A1 | 8/2010 | Taniguchi et al. | |
| 2010/0216793 A1 | 8/2010 | Alberati et al. | |
| 2012/0028951 A1 | 2/2012 | Taniguchi et al. | |
| 2012/0277204 A1 | 11/2012 | Taniguchi et al. | |
| 2012/0277430 A1 | 11/2012 | Taniguchi et al. | |
| 2012/0277431 A1 | 11/2012 | Taniguchi et al. | |
| 2013/0137675 A1 | 5/2013 | Taniguchi et al. | |
| 2013/0137700 A1 | 5/2013 | Hasui et al. | |
| 2013/0150344 A1 | 6/2013 | Yoshikawa et al. | |
| 2014/0178304 A1 | 6/2014 | Taniguchi et al. | |
| 2015/0099757 A1 | 4/2015 | Taniguchi et al. | |

FOREIGN PATENT DOCUMENTS

| | | | |
|---|---|---|---|
| WO | 2010/090737 | | 8/2010 |
| WO | 2010/094762 | | 8/2010 |
| WO | WO2010/090737 | * | 8/2010 |
| WO | 2012/018058 | | 2/2012 |
| WO | 2012/018059 | | 2/2012 |
| WO | 2012/020780 | | 2/2012 |
| WO | 2013/027845 | | 2/2013 |

OTHER PUBLICATIONS

Von Ulrich Schmidt, "Azopyridone Durch Kernsythese: Eine Neue Synthese Des Pyridoxols", Justus Liebigs Annalen de Chemie, 1962, 657, pp. 156-161.
Annali di Chimica (Rome, Italy) 1958, 48, pp. 1342-1348.
A.Z. El-Sonbati, et al., "Polymer complexes XLII. Supramolecular assemblies comprised of macrocyclic polymer complexes", Designed Monomers and Polymers, 2004, vol. 7, No. 5, pp. 445-459.
Ahmed T. Mubarak, et al., "Supramolecular structures and properties models of macrocyclic polymer complexes", Applied Organometallic Chemistry, 2004, 18(7), pp. 343-352.

* cited by examiner

PRODUCTION METHOD OF PYRIDAZINONE COMPOUNDS

TECHNICAL FIELD

The present invention relates to an industrially advantageous method of producing a pyridazinone compound.

BACKGROUND OF THE INVENTION

A pyridazinone compound represented by the following formula:

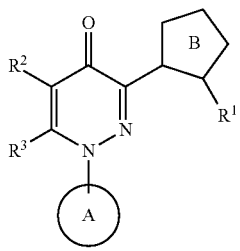

(I)

wherein
$R^1$ is a substituent,
$R^2$ is a hydrogen atom or a substituent,
$R^3$ is a hydrogen atom or a substituent,
Ring A is an aromatic ring which can be substituted, and
Ring B is a 5-membered heteroaromatic ring which can be substituted,
is known to have a high safety and a superior phosphodiesterase 10A inhibitory activity, which is useful as an agent for the prophylaxis or treatment of schizophrenia and the like (Patent Document 1).

As a production method of a pyridazinone compound, methods disclosed in Patent Documents 1 to 6 and non-Patent Documents 1 to 5 are known.

There is a demand for the provision of an advantageous method of producing a pyridazinone compound, which is suitable for industrial production.

DOCUMENT LIST

Patent Document

Patent Document 1: WO 2010/090737
Patent Document 2: WO 2010/094762
Patent Document 3: WO 2010/063610
Patent Document 4: WO 2012/018058
Patent Document 5: WO 2012/018059
Patent Document 6: WO 2012/020780

Non-Patent Document

Non-Patent Document 1: Journal of Heterocyclic Chemistry, 18(2), 333-334, 1981 Non-Patent Document 2: Justus Liebigs Annalen der Chemie, 1962, 657, 156-61
Non-Patent Document 3: Annali di Chimica (Rome, Italy) 1958, 48, 1342-1348
Non-Patent Document 4: Designed Monomers and Polymers, 2004, 7(5), 445-459
Non-Patent Document 5: Applied Organometallic Chemistry, 2004, 18(7), 343-352

SUMMARY OF THE INVENTION

Problems to be Solved by the Invention

The present invention aims to provide a new method of easily producing a pyridazinone compound represented by the following formula (I) or (I') in high yield and at a low cost, which is suitable for industrial production.

Means of Solving the Problems

The present inventors have found that, by employing a route via the compound represented by the following formula (Vb) or formula (V'b) (or formula (V) or formula (V')) from the compound represented by the following formula (II) as a starting material, which is an unsymmetric diketone, the pyridazinone compound represented by the following formula (I) or (I') can be easily produced in high yield, at a low cost, in a suitable method for industrial production, with regioselectivity due to the structure of the substituent, which resulted in the completion of the present invention.

Accordingly, the present invention is the followings:

[1] A method of producing a compound represented by the formula (I) or formula (I'):

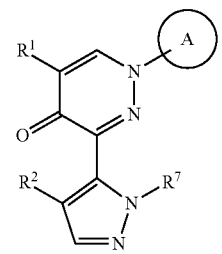

(I)

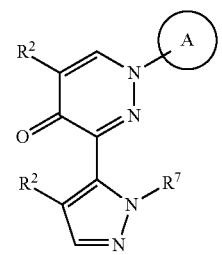

(I')

wherein
$R^1$ and $R^2$ are each independently a hydrogen atom or a substituent (excluding a benzyloxy group),
Ring A is an optionally substituted aromatic ring, and
$R^7$ is an optionally substituted hydrocarbon group or an optionally substituted heterocyclic group,
provided that a compound wherein $R^1$ and $R^2$ are same groups is excluded,
or a mixture thereof or a salt thereof (hereinafter to be referred to as compound (I) or compound (I') or a mixture thereof), which comprises
step (1): a step of reacting a compound represented by the formula (II):

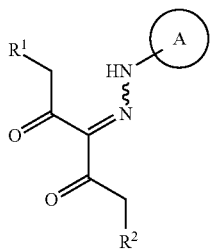

wherein each symbol is as defined above, or a salt thereof (hereinafter to be referred to as compound (II)), with a compound represented by the formula (IIIa):

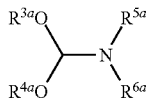

wherein $R^{3a}$, $R^{4a}$, $R^{5a}$ and $R^{6a}$ are each independently an optionally substituted hydrocarbon group, or a salt thereof (hereinafter to be referred to as compound (IIIa)), to give a compound represented by the formula (IV) or formula (IV'):

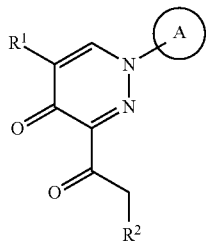

wherein each symbol is as defined above, or a mixture thereof or a salt thereof (hereinafter to be referred to as compound (IV) or compound (IV') or a mixture thereof);

step (2): a step of reacting the compound represented by the formula (IV) or formula (IV') or a mixture thereof or a salt thereof with a compound represented by the formula (IIIb):

wherein $R^{3b}$, $R^{4b}$, $R^{5b}$ and $R^{6b}$ are each independently an optionally substituted hydrocarbon group, or a salt thereof (hereinafter to be referred to as compound (IIIb)), to give a compound represented by the formula (Vb) or formula (V'b):

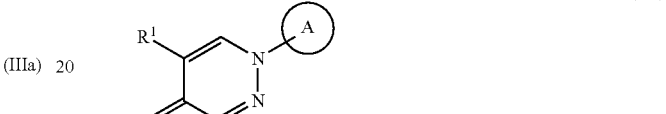

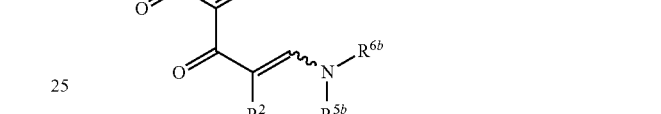

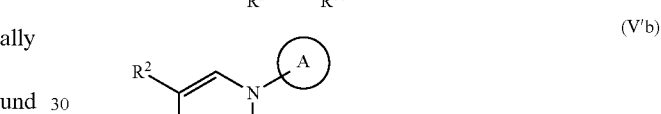

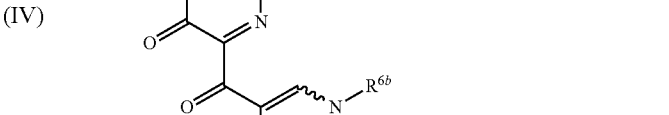

wherein each symbol is as defined above, or a mixture thereof or a salt thereof (hereinafter to be referred to as compound (Vb) or compound (V'b) or a mixture thereof); and step (3): a step of reacting the compound represented by formula (Vb) or formula (V'b) or a mixture thereof or a salt thereof, with a compound represented by the formula (VI):

$$R^7NH-NH_2 \quad (VI)$$

wherein each symbol is as defined above, or a salt thereof (hereinafter to be referred to as compound (VI)).

[2] A method of producing a compound represented by the formula (Vb) or formula (V'b):

-continued

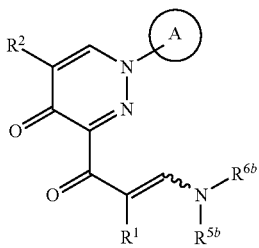
(V'b)

wherein
R¹ and R² are each independently a hydrogen atom or a substituent (excluding a benzyloxy group),
Ring A is an optionally substituted aromatic ring, and
R$^{5b}$ and R$^{6b}$ are each independently an optionally substituted hydrocarbon group,
provided that a compound wherein R¹ and R² are same groups is excluded,
or a mixture thereof or a salt thereof, which comprises step (1): a step of reacting a compound represented by formula (II):

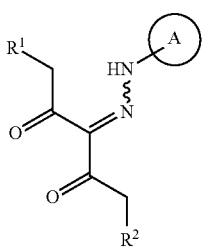
(II)

wherein each symbol is as defined above,
or a salt thereof, with a compound represented by the formula (IIIa):

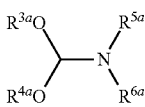
(IIIa)

wherein
R$^{3a}$, R$^{4a}$, R$^{5a}$ and R$^{6a}$ are each independently an optionally substituted hydrocarbon group,
or a salt thereof, to give a compound represented by the formula (IV) or formula (IV'):

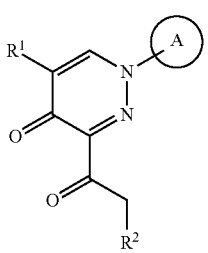
(IV)

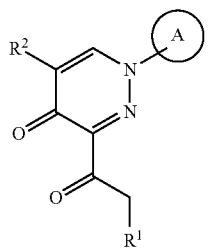
(IV')

wherein each symbol is as defined above,
or a mixture thereof or a salt thereof; and
step (2): a step of reacting the compound represented by the formula (IV) or formula (IV') or a mixture thereof or a salt thereof with a compound represented by formula (IIIb):

(IIIb)

R$^{3b}$O    R$^{5b}$
   \\  /
    N
   /  \\
R$^{4b}$O    R$^{6b}$ wherein R$^{3b}$ and R$^{4b}$ are each independently an optionally substituted hydrocarbon group, and the other symbols are as defined above,
or a salt thereof.
[3] The method of the above-mentioned [1] or [2], wherein the compound represented by the obtained formula (IV) or formula (IV') or a mixture thereof or a salt thereof obtained in step (1) is subjected to step (2) without isolation.
[4] A method of producing a compound represented by the formula (V) or formula (V'):

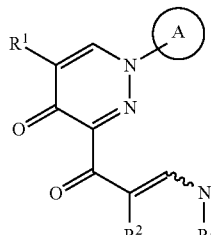
(V)

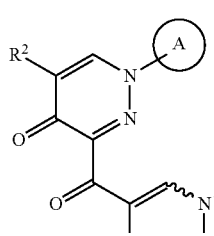
(V')

wherein
R¹ and R² are each independently a hydrogen atom or a substituent (excluding a benzyloxy group),
Ring A is an optionally substituted aromatic ring, and
R⁵ and R⁶ are each independently an optionally substituted hydrocarbon group,
provided that a compound wherein R¹ and R² are same groups is excluded, or a mixture thereof or a salt thereof (hereinafter to be referred to as compound (V) or compound (V') or a mixture thereof), which comprises step (1 and 2): a step of reacting a compound represented by the formula (II):

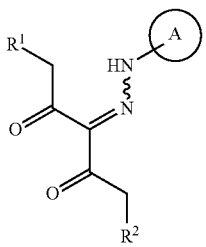

(II)

wherein each symbol is as defined above,
or a salt thereof, with a compound represented by the formula (III):

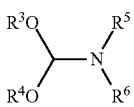

(III)

wherein $R^3$ and $R^4$ are each independently an optionally substituted hydrocarbon group, and the other symbols are as defined above,
or a salt thereof (hereinafter to be referred to as compound (III)).

[5] The method of any of the above-mentioned [1] to [3], wherein,
$R^1$ is an optionally substituted aromatic ring group, —$OR^8$, —$NHR^8$, —$NR^8R^{8'}$ or —$SR^8$ wherein $R^8$ and $R^{8'}$ are each independently an optionally substituted $C_{1-10}$ alkyl group, an optionally substituted $C_{2-10}$ alkenyl group, an optionally substituted $C_{2-10}$ alkynyl group, an optionally substituted $C_{3-10}$ cycloalkyl group, an optionally substituted $C_{3-10}$ cycloalkenyl group, an optionally substituted $C_{4-10}$ cycloalkadienyl group, an optionally substituted $C_{6-14}$ aryl group, an optionally substituted $C_{8-14}$ aralkyl group or an optionally substituted $C_{8-13}$ aryl alkenyl group,
$R^2$ is (1) a hydrogen atom, (2) an optionally substituted $C_{1-10}$ alkyl group, (3) an optionally substituted $C_{2-10}$ alkenyl group, (4) an optionally substituted $C_{2-10}$ alkynyl group, or (5) an optionally substituted $C_{3-10}$ cycloalkyl group, and the compound represented by the formula (IV) or a salt thereof is obtained in step (1).

[6] The method of any of the above-mentioned [1] to [5], wherein $R^1$ is methoxy, and $R^2$ is a hydrogen atom.

[7] The method of any of the above-mentioned [1], [3], [5] and [6], wherein Ring A is 4-(pyrazol-1-yl)-2-fluorobenzene, and $R^7$ is phenyl.

[8] A compound represented by the formula (IIa):

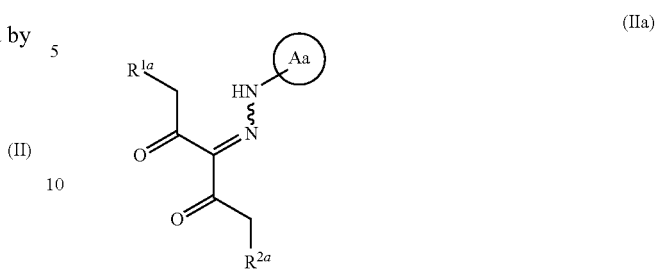

(IIa)

wherein
$R^{1a}$ is —$OR^9$ wherein $R^9$ is a substituent (excluding an ethenyl group and a benzyl group), and
$R^{2a}$ is a hydrogen atom or a substituent, and
Ring Aa is an optionally substituted aromatic ring, provided that
a compound wherein $R^{1a}$ and $R^{2a}$ are same groups is excluded, and 1-methoxy-3-(2-phenylhydrazinylidene)pentane-2,4-dione and 1-phenoxy-3-(2-phenylhydrazinylidene)pentane-2,4-dione are excluded,
or a salt thereof (hereinafter to be referred to as compound (IIa)).

[9] A compound represented by the formula:

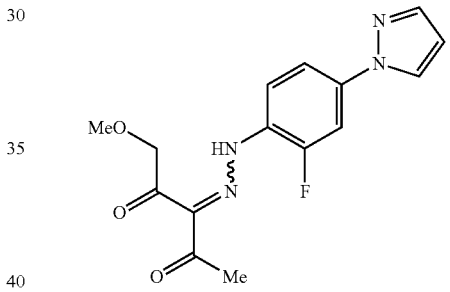

which is (3-{2-[2-fluoro-4-(1H-pyrazol-1-yl)phenyl]hydrazinylidene}-1-methoxypentane-2,4-dione) or a salt thereof.

Effect of the Invention

According to the present invention, from compound (II) as a starting material, which is an unsymmetric diketone, pyridazinone compound (I) or (I') can be easily produced in high yield, at a low cost, in a suitable method for industrial production, with regioselectivity due to the structure of the substituent.

DETAILED DESCRIPTION OF THE INVENTION

The "halogen atom" in the present specification, means a fluorine atom, a chlorine atom, a bromine atom or an iodine atom.

The "$C_{1-10}$ alkyl group" in the present specification means, for example, methyl, ethyl, propyl, isopropyl, butyl, 2-methylpropyl, 1-methylpropyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl or the like. Among them, a $C_{1-6}$ alkyl group is preferable.

The "$C_{1-6}$ alkyl (group)" in the present specification means, for example, methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl or the like.

The "$C_{2-10}$ alkenyl group" in the present specification means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl, 1-heptenyl, 1-octenyl or the like. Among them, a $C_{2-6}$ alkenyl group is preferable.

The "$C_{2-6}$ alkenyl (group)" in the present specification means, for example, vinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl or the like.

The "$C_{2-10}$ alkynyl group" in the present specification means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl, 1-heptynyl, 1-octynyl or the like. Among them, a $C_{2-6}$ alkynyl group is preferable.

The "$C_{2-6}$ alkynyl (group)" in the present specification means, for example, ethynyl, 1-propynyl, 2-propynyl, 1-butynyl, 2-butynyl, 3-butynyl, 1-pentynyl, 2-pentynyl, 3-pentynyl, 4-pentynyl, 1,1-dimethylprop-2-yn-1-yl, 1-hexynyl, 2-hexynyl, 3-hexynyl, 4-hexynyl, 5-hexynyl or the like.

The "$C_{1-6}$ alkoxy (group)" in the present specification means, for example, methoxy, ethoxy, propoxy, isopropoxy, butoxy, isobutoxy, sec-butoxy, tert-butoxy, pentyloxy, isopentyloxy, hexyloxy or the like.

The "$C_{2-6}$ alkenyloxy (group)" in the present specification means, for example, vinyloxy, 1-propenyloxy, 2-propenyloxy, 2-methyl-1-propenyloxy, 1-butenyloxy, 2-butenyloxy, 3-butenyloxy, 3-methyl-2-butenyloxy, 1-pentenyloxy, 2-pentenyloxy, 3-pentenyloxy, 4-pentenyloxy, 4-methyl-3-pentenyloxy, 1-hexenyloxy, 3-hexenyloxy, 5-hexenyloxy or the like.

The "$C_{2-6}$ alkynyloxy (group)" in the present specification means, for example, ethynyloxy, 1-propynyloxy, 2-propynyloxy, 1-butynyloxy, 2-butynyloxy, 3-butynyloxy, 1-pentynyloxy, 2-pentynyloxy, 3-pentynyloxy, 4-pentynyloxy, 1,1-dimethylprop-2-yn-1-yloxy, 1-hexynyloxy, 2-hexynyloxy, 3-hexynyloxy, 4-hexynyloxy, 5-hexynyloxy or the like.

The "$C_{1-6}$ alkylenedioxy (group)" in the present specification means, for example, methylenedioxy, ethylenedioxy or the like.

The "$C_{1-6}$ alkoxy-carbonyl (group)" in the present specification means, for example, methoxycarbonyl, ethoxycarbonyl, propoxycarbonyl, isopropoxycarbonyl, butoxycarbonyl, isobutoxycarbonyl, tert-butoxycarbonyl or the like.

The "$C_{1-6}$ alkyl-carbonyl (group)" in the present specification means, for example, acetyl, propanoyl, butanoyl, 2-methylpropanoyl or the like.

The "mono-$C_{1-6}$ alkyl amino (group)" in the present specification means, for example, methylamino, ethylamino, propylamino, isopropylamino, butylamino, isobutylamino, tert-butylamino or the like.

The "di-$C_{1-6}$ alkyl amino (group)" in the present specification means, for example, dimethylamino, diethylamino, dipropylamino, diisopropylamino, dibutylamino, diisobutylamino, ditert-butylamino or the like.

The "$C_{3-10}$ cycloalkyl (group)" in the present specification means, for example, cyclopropyl, cyclobutyl, cyclopentyl, cyclohexyl, cycloheptyl, cyclooctyl, cyclononyl, cyclodecyl or the like. Among them, a $C_{3-6}$ cycloalkyl group is preferable.

The "$C_{3-8}$ cycloalkyl (group)" in the present specification means, for example, cyclopropyl, cyclobutyl, cyclopentyl, cyclohexyl, cycloheptyl, cyclooctyl or the like.

The "$C_{3-6}$ cycloalkyl (group)" in the present specification means, for example, one having 3 to 6 carbon atoms, from among the above-mentioned $C_{3-8}$ cycloalkyl (group).

The "$C_{3-8}$ cycloalkyloxy (group)" in the present specification means, for example, cyclopropyloxy, cyclobutyloxy, cyclopentyloxy, cyclohexyloxy, cycloheptyloxy, cyclooctyloxy or the like.

The "$C_{3-6}$ cycloalkyloxy (group)" in the present specification means, for example, cyclopropyloxy, cyclobutyloxy, cyclopentyloxy, cyclohexyloxy or the like.

The "$C_{3-10}$ cycloalkenyl group" in the present specification means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 1-cyclohexen-1-yl, 2-cyclohexen-1-yl, 3-cyclohexen-1-yl), cycloheptenyl (e.g., 1-cyclopenten-1-yl, 2-cyclohepten-1-yl, 2-cyclohepten-1-yl), cyclooctenyl (e.g., 1-cycloocten-1-yl, 2-cycloocten-1-yl, 3-cycloocten-1-yl), cyclononenyl (e.g., 1-cyclononen-1-yl, 2-cyclononen-1-yl, 3-cyclononen-1-yl) or the like. Among them, a $C_{3-8}$ cycloalkenyl group is preferable.

The "$C_{3-8}$ cycloalkenyl (group)" in the present specification means, for example, cyclopropenyl (e.g., 2-cyclopropen-1-yl), cyclobutenyl (e.g., 2-cyclobuten-1-yl), cyclopentenyl (e.g., 2-cyclopenten-1-yl, 3-cyclopenten-1-yl), cyclohexenyl (e.g., 2-cyclohexen-1-yl, 3-cyclohexen-1-yl) or the like.

The "$C_{3-8}$ cycloalkenyloxy (group)" in the present specification means, for example, cyclopropenyloxy (e.g., 2-cyclopropen-1-yloxy), cyclobutenyloxy (e.g., 2-cyclobuten-1-yloxy), cyclopentenyloxy (e.g., 2-cyclopenten-1-yloxy, 3-cyclopenten-1-yloxy), cyclohexenyloxy (e.g., 2-cyclohexen-1-yloxy, 3-cyclohexen-1-yloxy) or the like.

The "$C_{4-10}$ cycloalkadienyl group" in the present specification means, for example, 1,3-cyclobutadien-1-yl, 1,3-cyclopentadien-1-yl, 1,4-cyclopentadien-1-yl, 2,4-cyclopentadien-1-yl, 1,3-cyclohexadien-1-yl, 1,4-cyclohexadien-1-yl, 1,5-cyclohexadien-1-yl, 2,4-cyclohexadien-1-yl, 2,5-cyclohexadien-1-yl, 1,3-cyclooctadien-1-yl, 1,4-cyclooctadien-1-yl, 1,5-cyclooctadien-1-yl, 1,6-cyclooctadien-1-yl, 1,7-cyclooctadien-1-yl, 2,4-cyclooctadien-1-yl, 2,5-cyclooctadien-1-yl, 2,6-cyclooctadien-1-yl, 2,7-cyclooctadien-1-yl, 3,5-cyclooctadien-1-yl, 3,6-cyclooctadien-1-yl or the like. Among them, a $C_{4-6}$ cycloalkadienyl group is preferable.

The "$C_{4-6}$ cycloalkadienyl group" in the present specification means, for example, 1,3-cyclobutadien-1-yl, 1,3-cyclopentadien-1-yl, 1,4-cyclopentadien-1-yl, 2,4-cyclopentadien-1-yl, 1,3-cyclohexadien-1-yl, 1,4-cyclohexadien-1-yl, 1,5-cyclohexadien-1-yl, 2,4-cyclohexadien-1-yl, 2,5-cyclohexadien-1-yl or the like.

The above-mentioned $C_{3-10}$ cycloalkyl group, $C_{3-10}$ cycloalkenyl group and $C_{4-10}$ cycloalkadienyl group each optionally form a fused ring group with a benzene ring. Examples of the fused ring group include indanyl, dihydronaphthyl, tetrahydronaphthyl, fluorenyl and the like.

In addition, the above-mentioned $C_{3-10}$ cycloalkyl group, $C_{3-10}$ cycloalkenyl group and $C_{4-10}$ cycloalkadienyl group are optionally a $C_{7-10}$ bridged hydrocarbon group. Examples of the $C_{7-10}$ bridged hydrocarbon group include bicyclo[2.2.1]heptyl(norbornyl), bicyclo[2.2.2]octyl, bicyclo[3.2.1]

octyl, bicyclo[3.2.2]nonyl, bicyclo[3.3.1]nonyl, bicyclo[4.2.1]nonyl, bicyclo[4.3.1]decyl, adamantyl and the like.

Moreover, the above-mentioned $C_{3-10}$ cycloalkyl group, $C_{3-10}$ cycloalkenyl group and $C_{4-10}$ cycloalkadienyl group each optionally form a spiro ring group with a $C_{3-10}$ cycloalkane, $C_{3-10}$ cycloalkene or $C_{4-10}$ cycloalkadiene. Examples of the $C_{3-10}$ cycloalkane, $C_{3-10}$ cycloalkene and $C_{4-10}$ cycloalkadiene include rings corresponding to the above-mentioned $C_{3-10}$ cycloalkyl group, $C_{3-10}$ cycloalkenyl group and $C_{4-10}$ cycloalkadienyl group. Examples of the spiro ring group include spiro[4.5]decan-8-yl and the like.

The "$C_{6-14}$ aryl (group)" in the present specification means, for example, phenyl, 1-naphthyl, 2-naphthyl or the like.

The "$C_{6-14}$ aryloxy (group)" in the present specification means, for example, phenoxy, 1-naphthyloxy, 2-naphthyloxy or the like.

The "$C_{7-14}$ aralkyl (group)" in the present specification means, for example, benzyl, phenethyl or the like.

The "$C_{8-14}$ aralkyl (group)" in the present specification means, for example, phenethyl or the like.

The "$C_{7-14}$ aralkyloxy (group)" in the present specification means, for example, benzyloxy, phenethyloxy or the like.

The "$C_{8-13}$ aryl alkenyl group" in the present specification means, for example, styryl or the like.

The "hydrocarbon group" in the present specification means, for example, a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-14}$ aralkyl group, a $C_{8-13}$ aryl alkenyl group or the like.

The "heterocyclic group" in the present specification means an aromatic heterocyclic group or a non-aromatic heterocyclic group.

The "aromatic heterocyclic group" in the present specification means a monocyclic aromatic heterocyclic group or a fused aromatic heterocyclic group, for example, a 5- to 12-membered aromatic heterocyclic group, specifically, a 5- to 7-membered monocyclic aromatic heterocyclic group or a 8- to 12-membered fused aromatic heterocyclic group.

The "monocyclic aromatic heterocyclic group" means, for example, a 5- to 7-membered (preferably 5- or 6-membered) monocyclic aromatic heterocyclic group ring containing, as a ring-constituting atom besides carbon atom, 1 to 4 hetero atoms selected from an oxygen atom, a sulfur atom (optionally oxidized) and a nitrogen atom (optionally oxidized), and examples thereof include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl) and the like.

The "fused aromatic heterocyclic group" in the present specification means, for example, a 8- to 12-membered fused aromatic heterocyclic group, specifically, a group derived from a fused ring formed by fusion of the ring corresponding to the above-mentioned 5- to 7-membered monocyclic aromatic heterocyclic group and a $C_{6-14}$ aromatic hydrocarbon; or a group derived from a fused ring formed by fusion of the ring corresponding to the above-mentioned 5- to 7-membered monocyclic aromatic heterocyclic groups, and examples thereof include quinolyl (e.g., 2-quinolyl, 3-quinolyl, 4-quinolyl, 6-quinolyl), isoquinolyl (e.g., 3-isoquinolyl), quinazolyl (e.g., 2-quinazolyl, 4-quinazolyl), quinoxalyl (e.g., 2-quinoxalyl, 6-quinoxalyl), benzofuranyl (e.g., 2-benzofuranyl, 3-benzofuranyl), benzothienyl (e.g., 2-benzothienyl, 3-benzothienyl), benzoxazolyl (e.g., 2-benzoxazolyl), benzisoxazolyl (e.g., 7-benzisoxazolyl), benzothiazolyl (e.g., 2-benzothiazolyl), benzimidazolyl (e.g., benzimidazol-1-yl, benzimidazol-2-yl, benzimidazol-5-yl), benzotriazolyl (e.g., 1H-1,2,3-benzotriazol-5-yl), indolyl (e.g., indol-1-yl, indol-2-yl, indol-3-yl, indol-5-yl), indazolyl (e.g., 1H-indazol-3-yl), pyrrolopyrazinyl (e.g., 1H-pyrrolo[2,3-b]pyrazin-2-yl, 1H-pyrrolo[2,3-b]pyrazin-6-yl), imidazopyridyl (e.g., 1H-imidazo[4,5-b]pyridin-2-yl, 1H-imidazo[4,5-c]pyridin-2-yl, 2H-imidazo[1,2-a]pyridin-3-yl), thienopyridyl (e.g., thieno[2,3-b]pyridin-3-yl), imidazopyrazinyl (e.g., 1H-imidazo[4,5-b]pyrazin-2-yl), pyrazolopyridyl (e.g., 1H-pyrazolo[4,3-c]pyridin-3-yl), pyrazolothienyl (e.g., 2H-pyrazolo[3,4-b]thiophen-2-yl), pyrazolotriazinyl (e.g., pyrazolo[5,1-c][1,2,4]triazin-3-yl) and the like.

The "non-aromatic heterocyclic group" in the present specification means a monocyclic non-aromatic heterocyclic group or a fused non-aromatic heterocyclic group, for example, a 3- to 12-membered non-aromatic heterocyclic group, specifically, a 3- to 8-membered monocyclic non-aromatic heterocyclic group or a 8- to 12-membered fused non-aromatic heterocyclic group.

The "monocyclic non-aromatic heterocyclic group" in the present specification means, for example, a 3- to 8-membered (preferably 5- or 6-membered) monocyclic non-aromatic heterocyclic group containing, as a ring-constituting atom besides carbon atom, 1 to 4 hetero atoms selected from an oxygen atom, a sulfur atom (optionally oxidized) and a nitrogen atom (optionally oxidized), and examples thereof include azetidinyl (e.g., 1-azetidinyl, 2-azetidinyl), pyrrolidinyl (e.g., 1-pyrrolidinyl, 2-pyrrolidinyl), piperidyl (e.g., piperidino, 2-piperidyl, 3-piperidyl, 4-piperidyl), morpholinyl (e.g., morpholino), thiomorpholinyl (e.g., thiomorpholino), piperazinyl (e.g., 1-piperazinyl, 2-piperazinyl, 3-piperazinyl), oxazolidinyl (e.g., oxazolidin-2-yl), thiazolidinyl (e.g., thiazolidin-2-yl), dihydrothiopyranyl (e.g., dihydrothiopyran-3-yl, dihydrothiopyran-4-yl), imidazolidinyl (e.g., imidazolidin-2-yl, imidazolidin-3-yl), oxazolinyl (e.g., oxazolin-2-yl), thiazolinyl (e.g., thiazolin-2-yl), imidazolinyl (e.g., imidazolin-2-yl, imidazolin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), pyranyl (e.g., 2-pyranyl, 4-pyranyl), tetrahydropyranyl (e.g., 2-tetrahydropyranyl, 3-tetrahydropyranyl, 4-tetrahydropyranyl), thiopyranyl (e.g., 4-thiopyranyl), tetrahydrothiopyranyl (e.g., 2-tetrahydrothiopyranyl, 3-tetrahydrothiopyranyl, 4-tetrahydrothiopyranyl), 1-oxidotetrahydrothiopyranyl (e.g., 1-oxidotetrahydrothiopyran-4-yl), 1,1-dioxidotetrahydrothiopyranyl (e.g., 1,1-dioxidotetrahydrothiopyran-4-yl), tetrahydrofuryl (e.g., tetrahydrofuran-3-yl, tetrahydrofuran-2-yl), oxetanyl (e.g., oxetan-2-yl, oxetan-3-yl), pyrazolidinyl (e.g., pyrazolidin-1-yl, pyrazolidin-3-yl), pyrazolinyl (e.g., pyrazolin-1-yl), tetrahydropyrimidinyl (e.g., tetrahydropyrimidin-1-yl), dihydrotriazolyl (e.g., 2,3-dihydro-1H-

1,2,3-triazol-1-yl), tetrahydrotriazolyl (e.g., 2,3,4,5-tetrahydro-1H-1,2,3-triazol-1-yl), azepanyl (e.g., 1-azepanyl, 2-azepanyl, 3-azepanyl, 4-azepanyl), dihydropyridyl (e.g., dihydropyridin-1-yl, dihydropyridin-2-yl, dihydropyridin-3-yl, dihydropyridin-4-yl), tetrahydropyridyl (e.g., 1,2,3,4-tetrahydropyridin-1-yl, 1,2,3,4-tetrahydropyridin-2-yl, 1,2,3,4-tetrahydropyridin-3-yl, 1,2,3,4-tetrahydropyridin-4-yl) and the like.

The "fused non-aromatic heterocyclic group" in the present specification means, for example, a 8- to 12-membered fused non-aromatic heterocyclic group, specifically, a group derived from a fused ring formed by fusion of the ring corresponding to the above-mentioned 3- to 8-membered monocyclic non-aromatic heterocyclic group and a $C_{6-14}$ aromatic hydrocarbon; a group derived from a fused ring formed by fusion of the ring corresponding to the above-mentioned 3- to 8-membered monocyclic non-aromatic heterocyclic groups; a group derived from a fused ring formed by fusion of the ring corresponding to the above-mentioned 3- to 8-membered monocyclic non-aromatic heterocycle and the ring corresponding to the above-mentioned 5- to 7-membered monocyclic aromatic heterocyclic group; or a partially saturated group thereof, and examples thereof dihydroindolyl (e.g., 2,3-dihydro-1H-indol-1-yl), dihydroisoindolyl (e.g., 1,3-dihydro-2H-isoindol-2-yl), dihydrobenzofuranyl (e.g., 2,3-dihydro-1-benzofuran-5-yl), tetrahydrobenzofuranyl (e.g., 4,5,6,7-tetrahydro-1-benzofuran-3-yl), dihydrobenzodioxinyl (e.g., 2,3-dihydro-1,4-benzodioxin-2-yl), dihydrobenzodioxepinyl (e.g., 3,4-dihydro-2H-1,5-benzodioxepin-2-yl), chromenyl (e.g., 4H-chromen-2-yl, 2H-chromen-3-yl), dihydrochromenyl (e.g., 3,4-dihydro-2H-chromen-2-yl), dihydroquinolyl (e.g., 1,2-dihydroquinolin-4-yl), tetrahydroquinolyl (e.g., 1,2,3,4-tetrahydroquinolin-4-yl), dihydroisoquinolyl (e.g., 1,2-dihydroisoquinolin-4-yl), tetrahydroisoquinolyl (e.g., 1,2,3,4-tetrahydroisoquinolin-4-yl), dihydrophthalazinyl (e.g., 1,4-dihydrophthalazin-4-yl) and the like.

The above-mentioned "monocyclic non-aromatic heterocyclic group" and "fused non-aromatic heterocyclic group" are optionally bridged, and examples thereof include 3-oxa-6-azabicyclo[3.1.1]heptyl, 8-oxa-3-azabicyclo[3.2.1]octyl, 2-oxa-5-azabicyclo[2.2.1]heptyl, 3-oxa-8-azabicyclo[3.2.1]octyl, 6-oxa-3-azabicyclo[3.1.1]heptyl and the like.

The "aromatic ring group" in the present specification means a $C_{6-14}$ aryl group or an aromatic heterocyclic group.

The "aromatic ring" in the present specification means a $C_{6-14}$ aromatic hydrocarbon or an aromatic heterocycle.

The "$C_{6-14}$ aromatic hydrocarbon" in the present specification means, for example, benzene or naphthalene.

The "aromatic heterocycle" in the present specification means a ring corresponding to the above-mentioned "aromatic heterocyclic group".

The "$C_{3-10}$ cycloalkane" in the present specification means, for example, cyclopropane, cyclobutane, cyclopentane, cyclohexane, cycloheptane, cyclooctane, cyclononane, cyclodecane or the like.

The "$C_{3-10}$ cycloalkene" in the present specification means, for example, cyclopropene, cyclobutene, cyclopentene, cyclohexene, cyclooctene, cyclononene, cyclodecene or the like.

The "$C_{4-10}$ cycloalkadiene" in the present specification means, for example, 1,3-cyclobutadiene, 1,3-cyclopentadiene, 1,4-cyclopentadiene, 2,4-cyclopentadiene, 1,3-cyclohexadiene, 1,4-cyclohexadiene, 1,5-cyclohexadiene, 2,4-cyclohexadiene, 2,5-cyclohexadiene, 1,3-cyclooctadiene, 1,4-cyclooctadiene, 1,5-cyclooctadiene, 1,6-cyclooctadiene, 1,7-cyclooctadiene, 2,4-cyclooctadiene, 2,5-cyclooctadiene, 2,6-cyclooctadiene, 2,7-cyclooctadiene, 3,5-cyclooctadiene, 3,6-cyclooctadiene or the like.

The definition of each symbol in the formulas is explained in the following.

$R^1$ and $R^2$ are each independently a hydrogen atom or a substituent (excluding a benzyloxy group).

Examples of the "substituent" for $R^1$ or $R^2$ include an optionally substituted hydrocarbon group, an optionally substituted heterocyclic group, an optionally substituted hydroxy group, an optionally substituted sulfanyl group, an optionally substituted amino group, an acyl group, a nitro group, a cyano group and a halogen atom.

The above-mentioned $C_{1-10}$ alkyl group, $C_{2-10}$ alkenyl group and $C_{2-10}$ alkynyl group exemplified as the "hydrocarbon group" optionally have 1 to 5 (preferably 1 to 3) substituents at substitutable position(s). Examples of the substituent include substituents selected from the following Substituent Group A. When the number of the substituents is plural, the respective substituents may be the same or different.

Substituent Group A:
(1) a halogen atom;
(2) a cyano group;
(3) a nitro group;
(4) a hydroxy group;
(5) a $C_{3-8}$ cycloalkyl group optionally substituted by 1 to 3 substituents selected from.
  (a) a halogen atom,
  (b) a cyano group,
  (c) a $C_{1-6}$ alkyl group optionally substituted by 1 to 3 halogen atoms, and
  (d) a $C_{1-6}$ alkoxy group optionally substituted by 1 to 3 halogen atoms;
(6) a $C_{6-14}$ aryl group optionally substituted by 1 to 3 substituents selected from
  (a) a halogen atom,
  (b) a cyano group,
  (c) a $C_{1-6}$ alkyl group optionally substituted by 1 to 3 halogen atoms, and
  (d) a $C_{1-6}$ alkoxy group optionally substituted by 1 to 3 halogen atoms;
(7) a $C_{1-6}$ alkoxy group optionally substituted by 1 to 3 substituents selected from
  (a) a halogen atom,
  (b) a cyano group,
  (c) a $C_{3-8}$ cycloalkyl group optionally substituted by 1 to 3 halogen atoms,
  (d) a $C_{3-8}$ cycloalkenyl group optionally substituted by 1 to 3 halogen atoms,
  (e) a $C_{6-14}$ aryl group optionally substituted by 1 to 3 halogen atoms, and
  (f) a 5- or 6-membered monocyclic aromatic heterocyclic group;
(8) a $C_{2-6}$ alkenyloxy group (e.g., vinyloxy, propenyloxy, butenyloxy, pentenyloxy, hexenyloxy) optionally substituted by 1 to 3 halogen atoms;
(9) a $C_{2-6}$ alkynyloxy group (e.g., ethynyloxy, propynyloxy, butynyloxy, pentynyloxy, hexynyloxy) optionally substituted by 1 to 3 halogen atoms;
(10) a $C_{3-8}$ cycloalkyloxy group (e.g., cyclopropyloxy, cyclobutyloxy, cyclopentyloxy, cyclohexyloxy) optionally substituted by 1 to 3 halogen atoms;
(11) a $C_{3-8}$ cycloalkenyloxy group (e.g., cyclopropenyloxy, cyclobutenyloxy, cyclopentenyloxy, cyclohexenyloxy) optionally substituted by 1 to 3 halogen atoms;
(12) a $C_{6-14}$ aryloxy group optionally substituted by 1 to 3 halogen atoms;

(13) a $C_{7-14}$ aralkyloxy group optionally substituted by 1 to 3 halogen atoms;
(14) a carbamoyl group optionally mono- or di-substituted by substituent(s) selected from
  (a) a $C_{1-6}$ alkyl group,
  (b) a $C_{3-6}$ cycloalkyl group,
  (c) a $C_{6-14}$ aryl group,
  (d) a $C_{1-6}$ alkoxy group,
  (e) a 5- or 6-membered monocyclic aromatic heterocyclic group,
  (f) a 8- to 12-membered fused aromatic heterocyclic group,
  (g) a 3- to 8-membered monocyclic non-aromatic heterocyclic group, and
  (h) a 8- to 12-membered fused non-aromatic heterocyclic group;
(15) a sulfamoyl group optionally mono- or di-substituted by substituent(s) selected from
  (a) a $C_{1-6}$ alkyl group,
  (b) a $C_{3-6}$ cycloalkyl group,
  (c) a $C_{6-14}$ aryl group,
  (d) a $C_{1-6}$ alkoxy group,
  (e) a 5- or 6-membered monocyclic aromatic heterocyclic group,
  (f) a 8- to 12-membered fused aromatic heterocyclic group,
  (g) a 3- to 8-membered monocyclic non-aromatic heterocyclic group, and
  (h) a 8- to 12-membered fused non-aromatic heterocyclic group;
(16) a formyl group;
(17) a $C_{1-6}$ alkyl-carbonyl group;
(18) a $C_{2-6}$ alkenyl-carbonyl group (e.g., acryloyl, butenoyl, pentenoyl, hexenoyl, heptenoyl);
(19) a $C_{2-6}$ alkynyl-carbonyl group (e.g., propioloyl, propynylcarbonyl, butynylcarbonyl, pentynylcarbonyl, hexynylcarbonyl);
(20) a $C_{3-8}$ cycloalkyl-carbonyl group (e.g., cyclopropylcarbonyl, cyclobutylcarbonyl, cyclopentylcarbonyl, cyclohexylcarbonyl);
(21) a $C_{3-8}$ cycloalkenyl-carbonyl group (e.g., cyclopropenylcarbonyl, cyclobutenylcarbonyl, cyclopentenylcarbonyl, cyclohexenylcarbonyl);
(22) a $C_{6-14}$ aryl-carbonyl group (e.g., benzoyl, 1-naphthylcarbonyl, 2-naphthylcarbonyl);
(23) a $C_{3-8}$ cycloalkyl-$C_{1-6}$ alkyl-carbonyl group (e.g., cyclopropylacetyl, 3-cyclopropylpropionyl, cyclobutylacetyl, cyclopentylacetyl, cyclohexylacetyl, cyclohexylpropionyl);
(24) a $C_{3-8}$ cycloalkenyl-$C_{1-6}$ alkyl-carbonyl group (e.g., cyclopentenylacetyl, cyclohexenylacetyl, 3-cyclohexenylpropionyl, 3-cyclohexenylpropionyl);
(25) a $C_{7-14}$ aralkyl-carbonyl group (e.g., phenylacetyl, 3-phenylpropionyl);
(26) a 5- or 6-membered monocyclic aromatic heterocyclylcarbonyl group (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl);
(27) a 8- to 12-membered fused aromatic heterocyclylcarbonyl group (e.g., benzofuranylcarbonyl, isobenzofuranylcarbonyl, benzothienylcarbonyl, isobenzothienylcarbonyl, indolylcarbonyl, isoindolylcarbonyl, indazolylcarbonyl, benzimidazolylcarbonyl, benzoxazolylcarbonyl);
(28) a 3- to 8-membered monocyclic non-aromatic heterocyclylcarbonyl group (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidylcarbonyl);
(29) a 8- to 12-membered fused non-aromatic heterocyclylcarbonyl group (e.g., dihydrobenzofuranylcarbonyl);
(30) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 halogen atoms,
  (c) a $C_{3-8}$ cycloalkyl-carbonyl group,
  (d) a $C_{6-14}$ aryl-carbonyl group optionally substituted by 1 to 3 halogen atoms,
  (e) a 5- or 6-membered monocyclic aromatic heterocyclylcarbonyl group,
  (f) a 8- to 12-membered fused aromatic heterocyclylcarbonyl group,
  (g) a 3- to 8-membered monocyclic non-aromatic heterocyclylcarbonyl group, and
  (h) a 8- to 12-membered fused non-aromatic heterocyclylcarbonyl group;
(31) a sulfanyl group;
(32) a $C_{1-6}$ alkylsulfanyl group (e.g., methylsulfanyl, ethylsulfanyl);
(33) a $C_{2-6}$ alkenylsulfanyl group (e.g., vinylsulfanyl, propenylsulfanyl);
(34) a $C_{2-6}$ alkynylsulfanyl group (e.g., ethynylsulfanyl, propynylsulfanyl);
(35) a $C_{3-8}$ cycloalkylsulfanyl group (e.g., cyclopropylsulfanyl, cyclobutylsulfanyl);
(36) a $C_{3-8}$ cycloalkenylsulfanyl group (e.g., cyclopropenylsulfanyl, cyclobutenylsulfanyl);
(37) a $C_{6-14}$ arylsulfanyl group (e.g., phenylsulfanyl);
(38) a $C_{3-8}$ cycloalkyl-$C_{1-6}$ alkylsulfanyl group (e.g., cyclopropylmethylsulfanyl);
(39) a $C_{3-8}$ cycloalkenyl-$C_{1-6}$ alkylsulfanyl group (e.g., cyclopentenylmethylsulfanyl);
(40) a $C_{1-6}$ alkylsulfinyl group (e.g., methylsulfinyl, ethylsulfinyl);
(41) a $C_{2-6}$ alkenylsulfinyl group (e.g., vinylsulfinyl, propenylsulfinyl);
(42) a $C_{2-6}$ alkynylsulfinyl group (e.g., ethynylsulfinyl, propynylsulfinyl);
(43) a $C_{3-8}$ cycloalkylsulfinyl group (e.g., cyclopropylsulfinyl, cyclobutylsulfinyl);
(44) a $C_{3-8}$ cycloalkenylsulfinyl group (e.g., cyclopropenylsulfinyl, cyclobutenylsulfinyl);
(45) a $C_{6-14}$ arylsulfinyl group (e.g., phenylsulfinyl);
(46) a $C_{3-8}$ cycloalkyl-$C_{1-6}$ alkylsulfinyl group (e.g., cyclopropylmethylsulfinyl);
(47) a $C_{3-8}$ cycloalkenyl-$C_{1-6}$ alkylsulfinyl group (e.g., cyclopentenylmethylsulfinyl);
(48) a $C_{1-6}$ alkylsulfonyl group (e.g., methylsulfonyl, ethylsulfonyl);
(49) a $C_{2-6}$ alkenylsulfonyl group (e.g., vinylsulfonyl, propenylsulfonyl);
(50) a $C_{2-6}$ alkynylsulfonyl group (e.g., ethynylsulfonyl, propynylsulfonyl);
(51) a $C_{3-8}$ cycloalkylsulfonyl group (e.g., cyclopropylsulfonyl, cyclobutylsulfonyl);
(52) a $C_{3-8}$ cycloalkenylsulfonyl group (e.g., cyclopropenylsulfonyl, cyclobutenylsulfonyl);
(53) a $C_{6-14}$ arylsulfonyl group (e.g., phenylsulfonyl);
(54) a $C_{3-8}$ cycloalkyl-$C_{1-6}$ alkylsulfonyl group (e.g., cyclopropylmethylsulfonyl);

(55) a $C_{3-8}$ cycloalkenyl-$C_{1-6}$ alkylsulfonyl group (e.g., cyclopentenylmethylsulfonyl);
(56) a $C_{6-14}$ aryl-$C_{1-6}$ alkylsulfonyl group (e.g., benzylsulfonyl);
(57) a 5- or 6-membered monocyclic aromatic heterocyclylsulfonyl group (e.g., furylsulfonyl, thienylsulfonyl, pyridylsulfonyl);
(58) a 8- to 12-membered fused aromatic heterocyclylsulfonyl group (e.g., benzofuranylsulfonyl, isobenzofuranylsulfonyl);
(59) a 3- to 8-membered monocyclic non-aromatic heterocyclylsulfonyl group (e.g., oxiranylsulfonyl, azetidinylsulfonyl);
(60) a 8- to 12-membered fused non-aromatic heterocyclylsulfonyl group (e.g., dihydrobenzofuranylsulfonyl);
(61) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl, morpholinyl) optionally substituted by 1 to 3 substituents selected from
  (a) a halogen atom,
  (b) a $C_{1-6}$ alkyl group optionally substituted by 1 to 3 halogen atoms, and
  (c) a $C_{1-6}$ alkoxy group optionally substituted by 1 to 3 halogen atoms;
(62) a 8- to 12-membered fused aromatic heterocyclic group (e.g., benzofuranyl, isobenzofuranyl, benzothienyl, isobenzothienyl, indolyl, isoindolyl, indazolyl, benzimidazolyl, benzoxazolyl) optionally substituted by 1 to 3 substituents selected from
  (a) a halogen atom,
  (b) a $C_{1-6}$ alkyl group optionally substituted by 1 to 3 halogen atoms, and
  (c) a $C_{1-6}$ alkoxy group optionally substituted by 1 to 3 halogen atoms;
(63) a 3- to 8-membered monocyclic non-aromatic heterocyclic group (e.g., oxiranyl, azetidinyl, oxetanyl, thietanyl, pyrrolidinyl, tetrahydrofuryl, thiolanyl, piperidyl, piperazinyl, dihydrooxadiazolyl, thiazolinyl) optionally substituted by 1 to 3 substituents selected from
  (a) a halogen atom,
  (b) a $C_{1-6}$ alkyl group optionally substituted by 1 to 3 halogen atoms,
  (c) a $C_{1-6}$ alkoxy group optionally substituted by 1 to 3 halogen atoms, and
  (d) an oxo group;
(64) a 8- to 12-membered fused non-aromatic heterocyclic group (e.g., dihydrobenzofuranyl) optionally substituted by 1 to 3 substituents selected from
  (a) a halogen atom,
  (b) a $C_{1-6}$ alkyl group optionally substituted by 1 to 3 halogen atoms,
  (c) a $C_{1-6}$ alkoxy group optionally substituted by 1 to 3 halogen atoms, and
  (d) an oxo group;
(65) a 5- or 6-membered monocyclic aromatic heterocyclyloxy group (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy);
(66) a 8- to 12-membered fused aromatic heterocyclyloxy group (e.g., benzofuranyloxy, isobenzofuranyloxy, benzothienyloxy, isobenzothienyloxy, indolyloxy, isoindolyloxy, indazolyloxy, benzimidazolyloxy, benzoxazolyloxy);
(67) a 3- to 8-membered monocyclic non-aromatic heterocyclyloxy group (e.g., oxiranyloxy, azetidinyloxy, oxetanyloxy, thietanyloxy, pyrrolidinyloxy, tetrahydrofuryloxy, thiolanyloxy, piperidyloxy);
(68) a 8- to 12-membered fused non-aromatic heterocyclyloxy group (e.g., dihydrobenzofuranyloxy);
(69) a carboxy group;
(70) a $C_{1-6}$ alkoxy-carbonyl group;
(71) a $C_{2-6}$ alkenyloxy-carbonyl group (e.g., vinyloxycarbonyl, propenyloxycarbonyl, butenyloxycarbonyl, pentenyloxycarbonyl, hexenyloxycarbonyl);
(72) a $C_{2-6}$ alkynyloxy-carbonyl group (e.g., ethynyloxycarbonyl, propynyloxycarbonyl, butynyloxycarbonyl, pentynyloxycarbonyl, hexynyloxycarbonyl);
(73) a $C_{3-8}$ cycloalkyloxy-carbonyl group (e.g., cyclopropyloxycarbonyl, cyclobutyloxycarbonyl, cyclopentyloxycarbonyl, cyclohexyloxycarbonyl);
(74) a $C_{3-8}$ cycloalkenyloxy-carbonyl group (e.g., cyclopropenyloxycarbonyl, cyclobutenyloxycarbonyl, cyclopentenyloxycarbonyl, cyclohexenyloxycarbonyl);
(75) a $C_{6-14}$ aryloxy-carbonyl group (e.g., phenoxycarbonyl, 1-naphthyloxycarbonyl, 2-naphthyloxycarbonyl);
(76) a $C_{3-8}$ cycloalkyl-$C_{1-6}$ alkoxy-carbonyl group (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl);
(77) a $C_{3-8}$ cycloalkenyl-$C_{1-6}$ alkoxy-carbonyl group (e.g., cyclopentenylmethyloxycarbonyl, cyclohexenylmethyloxycarbonyl, cyclohexenylethyloxycarbonyl, cyclohexenylpropyloxycarbonyl);
(78) a $C_{7-14}$ aralkyloxy-carbonyl group (e.g., benzyloxycarbonyl, phenethyloxycarbonyl);
(79) a mono-$C_{1-6}$ alkyl-thiocarbamoyl group (e.g., methylthiocarbamoyl, ethylthiocarbamoyl, propylthiocarbamoyl);
(80) a di-$C_{1-6}$ alkyl-thiocarbamoyl group (e.g., dimethylthiocarbamoyl, diethylthiocarbamoyl, dipropylthiocarbamoyl);
(81) a $C_{1-6}$ alkyl-carbonyloxy group (e.g., acetyloxy, propanoyloxy, butanoyloxy, 2-methylpropanoyloxy);
(82) an imino group optionally substituted by a hydroxy group; and
(83) a $C_{1-6}$ alkylenedioxy group (e.g., methylenedioxy, ethylenedioxy).

The above-mentioned $C_{3-10}$ cycloalkyl group, $C_{3-10}$ cycloalkenyl group and $C_{4-10}$ cycloalkadienyl group exemplified as the "hydrocarbon group" optionally have 1 to 5 (preferably 1 to 3) substituents at substitutable position(s). Examples of the substituent include substituents selected from the following Substituent Group B. When the number of the substituents is plural, the respective substituents may be the same or different.

Substituent Group B:
(1) the above-mentioned Substituent Group A;
(2) a $C_{1-6}$ alkyl group optionally substituted by 1 to 3 substituents selected from
  (a) a halogen atom,
  (b) a cyano group,
  (c) a hydroxy group,
  (d) a $C_{3-8}$ cycloalkyl group optionally substituted by 1 to 3 substituents selected from
    (i) a halogen atom,
    (ii) a cyano group, and
    (iii) a $C_{1-6}$ alkyl group optionally substituted by 1 to 3 halogen atoms, (e) a $C_{6-14}$ aryl group optionally substituted by 1 to 3 substituents selected from
  (i) a halogen atom,
  (ii) a cyano group, and
  (iii) a $C_{1-6}$ alkyl group optionally substituted by 1 to 3 halogen atoms,
(f) a $C_{1-6}$ alkoxy group optionally substituted by 1 to 3 halogen atoms,
(g) an amino group optionally mono or di-substituted by $C_{1-6}$ alkyl group(s),
(h) a 5- or 6-membered monocyclic aromatic heterocyclic group,
(i) a 8- to 12-membered fused aromatic heterocyclic group,
(j) a 3- to 8-membered monocyclic non-aromatic heterocyclic group,
(k) a 8- to 12-membered fused non-aromatic heterocyclic group,
(l) a carboxy group, and
(m) a $C_{1-6}$ alkoxy-carbonyl group optionally substituted by 1 to 3 halogen atoms;
(3) $C_{2-6}$ alkenyl group optionally substituted by 1 to 3 substituents selected from
  (a) a halogen atom,
  (b) a hydroxy group,
  (c) a $C_{1-6}$ alkoxy group,
  (d) an amino group optionally mono or di-substituted by $C_{1-6}$ alkyl group(s),
  (e) a carboxy group, and
  (f) a $C_{1-6}$ alkoxy-carbonyl group;
(4) $C_{7-14}$ aralkyl group optionally substituted by 1 to 3 substituents selected from
  (a) a halogen atom,
  (b) a hydroxy group,
  (c) a $C_{1-6}$ alkoxy group, and
  (d) a $C_{1-6}$ alkyl group optionally substituted by 1 to 3 halogen atoms; and
(5) an oxo group.

The above-mentioned $C_{6-14}$ aryl group, $C_{7-14}$ aralkyl group and $C_{8-13}$ aryl alkenyl group exemplified as the "hydrocarbon group" optionally have 1 to 5 (preferably 1 to 3) substituents at substitutable position(s). Examples of the substituent include substituents selected from the above-mentioned Substituent Group B excluding an oxo group. When the number of the substituents is plural, the respective substituents may be the same or different.

The "heterocyclic group" of the "optionally substituted heterocyclic group" exemplified as the "substituent" for $R^1$ or $R^2$ optionally has 1 to 5 (preferably 1 to 3) substituents at substitutable position(s). Examples of the substituent for the aromatic heterocyclic group include substituents selected from the above-mentioned Substituent Group B excluding an oxo group, and examples of the substituent for the non-aromatic heterocyclic group include substituents selected from the above-mentioned Substituent Group B. When the number of the substituents is plural, the respective substituents may be the same or different.

Examples of the "optionally substituted hydroxy group" exemplified as the "substituent" for $R^1$ or $R^2$ include a hydroxy group optionally substituted by a substituent selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{8-14}$ aralkyl group, a $C_{8-13}$ aryl alkenyl group, a $C_{1-6}$ alkyl-carbonyl group, a heterocyclic group (e.g., an aromatic heterocyclic group, a non-aromatic heterocyclic group) and the like, each of which is optionally substituted.

The $C_{1-10}$ alkyl group optionally has 1 to 5 (preferably 1 to 3) substituents at substitutable position(s). Examples of the substituent include
(1) a halogen atom;
(2) a cyano group;
(3) a nitro group;
(4) a hydroxy group;
(5) a $C_{3-8}$ cycloalkyl group optionally substituted by 1 to 3 substituents selected from
  (a) a halogen atom,
  (b) a cyano group,
  (c) a $C_{1-6}$ alkyl group optionally substituted by 1 to 3 halogen atoms, and
  (d) a $C_{1-6}$ alkoxy group optionally substituted by 1 to 3 halogen atoms;
(6) a $C_{7-14}$ aryl group optionally substituted by 1 to 3 substituents selected from
  (a) a halogen atom,
  (b) a cyano group,
  (c) a $C_{1-6}$ alkyl group optionally substituted by 1 to 3 halogen atoms, and
  (d) a $C_{1-6}$ alkoxy group optionally substituted by 1 to 3 halogen atoms;
(7) a $C_{1-6}$ alkoxy group optionally substituted by 1 to 3 substituents selected from
  (a) a halogen atom,
  (b) a cyano group,
  (c) a $C_{3-8}$ cycloalkyl group optionally substituted by 1 to 3 halogen atoms,
  (d) a $C_{3-8}$ cycloalkenyl group optionally substituted by 1 to 3 halogen atoms,
  (e) a $C_{6-14}$ aryl group optionally substituted by 1 to 3 halogen atoms, and
  (f) a 5- or 6-membered monocyclic aromatic heterocyclic group;
(8) a $C_{2-6}$ alkenyloxy group (e.g., vinyloxy, propenyloxy, butenyloxy, pentenyloxy, hexenyloxy) optionally substituted by 1 to 3 halogen atoms;
(9) a $C_{2-6}$ alkynyloxy group (e.g., ethynyloxy, propynyloxy, butynyloxy, pentynyloxy, hexynyloxy) optionally substituted by 1 to 3 halogen atoms;
(10) a $C_{3-8}$ cycloalkyloxy group (e.g., cyclopropyloxy, cyclobutyloxy, cyclopentyloxy, cyclohexyloxy) optionally substituted by 1 to 3 halogen atoms;
(11) a $C_{3-8}$ cycloalkenyloxy group (e.g., cyclopropenyloxy, cyclobutenyloxy, cyclopentenyloxy, cyclohexenyloxy) optionally substituted by 1 to 3 halogen atoms;
(12) a $C_{6-14}$ aryloxy group optionally substituted by 1 to 3 halogen atoms;
(13) a $C_{7-14}$ aralkyloxy group optionally substituted by 1 to 3 halogen atoms;
(14) a carbamoyl group optionally mono- or di-substituted by substituent(s) selected from
  (a) a $C_{1-6}$ alkyl group,
  (b) a $C_{3-6}$ cycloalkyl group,
  (c) a $C_{6-14}$ aryl group,
  (d) a $C_{1-6}$ alkoxy group,
  (e) a 5- or 6-membered monocyclic aromatic heterocyclic group,
  (f) a 8- to 12-membered fused aromatic heterocyclic group,
  (g) a 3- to 8-membered monocyclic non-aromatic heterocyclic group, and
  (h) a 8- to 12-membered fused non-aromatic heterocyclic group;
(15) a sulfamoyl group optionally mono- or di-Substituted by substituent(s) selected from (a) a $C_{1-6}$ alkyl group,
(b) a $C_{3-6}$ cycloalkyl group,
(c) a $C_{6-14}$ aryl group,
(d), a $C_{1-6}$ alkoxy group,
(e) a 5- or 6-membered monocyclic aromatic heterocyclic group,
(f) a 8- to 12-membered fused aromatic heterocyclic group,
(g) a 3- to 8-membered monocyclic non-aromatic heterocyclic group, and
(h) a 8- to 12-membered fused non-aromatic heterocyclic group;
(16) a formyl group;
(17) a $C_{1-6}$ alkyl-carbonyl group;
(18) a $C_{2-6}$ alkenyl-carbonyl group (e.g., acryloyl, butenoyl, pentenoyl, hexenoyl, heptenoyl);
(19) a $C_{2-6}$ alkynyl-carbonyl group (e.g., propioloyl, propynylcarbonyl, butynylcarbonyl, pentynylcarbonyl, hexynylcarbonyl);
(20) a $C_{3-8}$ cycloalkyl-carbonyl group (e.g., cyclopropylcarbonyl, cyclobutylcarbonyl, cyclopentylcarbonyl, cyclohexylcarbonyl);
(21) a $C_{3-8}$ cycloalkenyl-carbonyl group (e.g., cyclopropenylcarbonyl, cyclobutenylcarbonyl, cyclopentenylcarbonyl, cyclohexenylcarbonyl);
(22) a $C_{6-14}$ aryl-carbonyl group (e.g., benzoyl, 1-naphthylcarbonyl, 2-naphthylcarbonyl);
(23) a $C_{3-8}$ cycloalkyl-$C_{1-6}$ alkyl-carbonyl group (e.g., cyclopropylacetyl, 3-cyclopropylpropionyl, cyclobutylacetyl, cyclopentylacetyl, cyclohexylacetyl, cyclohexylpropionyl);
(24) a $C_{3-8}$ cycloalkenyl-$C_{1-6}$ alkyl-carbonyl group (e.g., cyclopentenylacetyl, cyclohexenylacetyl, 3-cyclohexenylpropionyl, 3-cyclohexenylpropionyl);
(25) a $C_{7-14}$ aralkyl-carbonyl group (e.g., phenylacetyl, 3-phenylpropionyl);
(26) a 5- or 6-membered monocyclic aromatic heterocyclylcarbonyl group (e.g., furylcarbonyl, thienylcarbonyl, pyrrolylcarbonyl, oxazolylcarbonyl, isoxazolylcarbonyl, thiazolylcarbonyl, isothiazolylcarbonyl, imidazolylcarbonyl, pyridylcarbonyl, pyrazolylcarbonyl);
(27) a 8- to 12-membered fused aromatic heterocyclylcarbonyl group (e.g., benzofuranylcarbonyl, isobenzofuranylcarbonyl, benzothienylcarbonyl, isobenzothienylcarbonyl, indolylcarbonyl, isoindolylcarbonyl, indazolylcarbonyl, benzimidazolylcarbonyl, benzoxazolylcarbonyl);
(28) a 3- to 8-membered monocyclic non-aromatic heterocyclylcarbonyl group (e.g., oxiranylcarbonyl, azetidinylcarbonyl, oxetanylcarbonyl, thietanylcarbonyl, pyrrolidinylcarbonyl, tetrahydrofurylcarbonyl, thiolanylcarbonyl, piperidylcarbonyl);
(29) a 8- to 12-membered fused non-aromatic heterocyclylcarbonyl group (e.g., dihydrobenzofuranylcarbonyl);
(30) an amino group optionally mono- or di-substituted by substituent(s) selected from
    (a) a $C_{1-6}$ alkyl group optionally substituted by 1 to 3 halogen atoms,
    (b) a $C_{1-6}$ alkyl-carbonyl group optionally substituted by 1 to 3 halogen atoms,
    (c) a $C_{3-8}$ cycloalkyl-carbonyl group,
    (d) a $C_{6-14}$ aryl-carbonyl group optionally substituted by 1 to 3 halogen atoms,
    (e) a 5- or 6-membered monocyclic aromatic heterocyclylcarbonyl group,
    (f) a 8- to 12-membered fused aromatic heterocyclylcarbonyl group,
    (g) a 3- to 8-membered monocyclic non-aromatic heterocyclylcarbonyl group, and
    (h) a 8- to 12-membered fused non-aromatic heterocyclylcarbonyl group;
(31) a sulfanyl group;
(32) a $C_{1-6}$ alkylsulfanyl group (e.g., methylsulfanyl, ethylsulfanyl);
(33) a $C_{2-6}$ alkenylsulfanyl group (e.g., vinylsulfanyl, propenylsulfanyl);
(34) a $C_{2-6}$ alkynylsulfanyl group (e.g., ethynylsulfanyl, propynylsulfanyl);
(35) a $C_{3-8}$ cycloalkylsulfanyl group (e.g., cyclopropylsulfanyl, cyclobutylsulfanyl);
(36) a $C_{3-8}$ cycloalkenylsulfanyl group (e.g., cyclopropenylsulfanyl, cyclobutenylsulfanyl);
(37) a $C_{6-14}$ arylsulfanyl group (e.g., phenylsulfanyl);
(38) a $C_{3-8}$ cycloalkyl-$C_{1-6}$ alkylsulfanyl group (e.g., cyclopropylmethylsulfanyl);
(39) a $C_{3-8}$ cycloalkenyl-$C_{1-6}$ alkylsulfanyl group (e.g., cyclopentenylmethylsulfanyl);
(40) a $C_{1-6}$ alkylsulfinyl group (e.g., methylsulfinyl, ethylsulfinyl);
(41) a $C_{2-6}$ alkenylsulfinyl group (e.g., vinylsulfinyl, propenylsulfinyl);
(42) a $C_{2-6}$ alkynylsulfinyl group (e.g., ethynylsulfinyl, propynylsulfinyl);
(43) a $C_{3-8}$ cycloalkylsulfinyl group (e.g., cyclopropylsulfinyl, cyclobutylsulfinyl);
(44) a $C_{3-8}$ cycloalkenylsulfinyl group (e.g., cyclopropenylsulfinyl, cyclobutenylsulfinyl);
(45) a $C_{6-14}$ arylsulfinyl group (e.g., phenylsulfinyl);
(46) a $C_{3-8}$ cycloalkyl-$C_{1-6}$ alkylsulfinyl group (e.g., cyclopropylmethylsulfinyl);
(47) a $C_{3-8}$ cycloalkenyl-$C_{1-6}$ alkylsulfinyl group (e.g., cyclopentenylmethylsulfinyl);
(48) a $C_{1-6}$ alkylsulfonyl group (e.g., methylsulfonyl, ethylsulfonyl);
(49) a $C_{2-6}$ alkenylsulfonyl group (e.g., vinylsulfonyl, propenylsulfonyl);
(50) a $C_{2-6}$ alkynylsulfonyl group (e.g., ethynylsulfonyl, propynylsulfonyl);
(51) a $C_{3-8}$ cycloalkylsulfonyl group (e.g., cyclopropylsulfonyl, cyclobutylsulfonyl);
(52) a $C_{3-8}$ cycloalkenylsulfonyl group (e.g., cyclopropenylsulfonyl, cyclobutenylsulfonyl);
(53) a $C_{6-14}$ arylsulfonyl group (e.g., phenylsulfonyl);
(54) a $C_{3-8}$ cycloalkyl-$C_{1-6}$ alkylsulfonyl group (e.g., cyclopropylmethylsulfonyl);
(55) a $C_{3-8}$ cycloalkenyl-$C_{1-6}$ alkylsulfonyl group (e.g., cyclopentenylmethylsulfonyl);
(56) a $C_{6-14}$ aryl-$C_{1-6}$ alkylsulfonyl group (e.g., benzylsulfonyl);
(57) a 5- or 6-membered monocyclic aromatic heterocyclylsulfonyl group (e.g., furylsulfonyl, thienylsulfonyl, pyridylsulfonyl);
(58) a 8- to 12-membered fused aromatic heterocyclylsulfonyl group (e.g., benzofuranylsulfonyl, isobenzofuranylsulfonyl);
(59) a 3- to 8-membered monocyclic non-aromatic heterocyclylsulfonyl group (e.g., oxiranylsulfonyl, azetidinylsulfonyl);
(60) a 8- to 12-membered fused non-aromatic heterocyclylsulfonyl group (e.g., dihydrobenzofuranylsulfonyl);
(61) a 5- or 6-membered monocyclic aromatic heterocyclic group (e.g., furyl, thienyl, pyrrolyl, oxazolyl, isoxazolyl, thiazolyl, isothiazolyl, imidazolyl, pyridyl, pyrazolyl, morpholinyl) optionally substituted by 1 to 3 substituents selected from
(a) a halogen atom,
(b) a $C_{1-6}$ alkyl group optionally substituted by 1 to 3 halogen atoms, and
(c) a $C_{1-6}$ alkoxy group optionally substituted by 1 to 3 halogen atoms;
(62) a 8- to 12-membered fused aromatic heterocyclic group (e.g., benzofuranyl, isobenzofuranyl, benzothienyl, isobenzothienyl, indolyl, isoindolyl, indazolyl, benzimidazolyl, benzoxazolyl) optionally substituted by 1 to 3 substituents selected from
(a) a halogen atom,
(b) a $C_{1-6}$ alkyl group optionally substituted by 1 to 3 halogen atoms, and
(c) a $C_{1-6}$ alkoxy group optionally substituted by 1 to 3 halogen atoms;
(63) a 3- to 8-membered monocyclic non-aromatic heterocyclic group (e.g., oxiranyl, azetidinyl, oxetanyl, thietanyl, pyrrolidinyl, tetrahydrofuryl, thiolanyl, piperidyl, piperazinyl, dihydrooxadiazolyl, thiazolinyl) optionally substituted by 1 to 3 substituents selected from
(a) a halogen atom,
(b) a $C_{1-6}$ alkyl group optionally substituted by 1 to 3 halogen atoms,
(c) a $C_{1-6}$ alkoxy group optionally substituted by 1 to 3 halogen atoms, and
(d) an oxo group;
(64) a 8- to 12-membered fused non-aromatic heterocyclic group (e.g., dihydrobenzofuranyl) optionally substituted by 1 to 3 substituents selected from
(a) a halogen atom,
(b) a $C_{1-6}$ alkyl group optionally substituted by 1 to 3 halogen atoms,
(c) a $C_{1-6}$ alkoxy group optionally substituted by 1 to 3 halogen atoms, and
(d) an oxo group;
(65) a 5- or 6-membered monocyclic aromatic heterocyclyloxy group (e.g., furyloxy, thienyloxy, pyrrolyloxy, oxazolyloxy, isoxazolyloxy, thiazolyloxy, isothiazolyloxy, imidazolyloxy, pyridyloxy, pyrazolyloxy);
(66) a 8- to 12-membered fused aromatic heterocyclyloxy group (e.g., benzofuranyloxy, isobenzofuranyloxy, benzothienyloxy, isobenzothienyloxy, indolyloxy, isoindolyloxy, indazolyloxy, benzimidazolyloxy, benzoxazolyloxy);
(67) a 3- to 8-membered monocyclic non-aromatic heterocyclyloxy group (e.g., oxiranyloxy, azetidinyloxy, oxetanyloxy, thietanyloxy, pyrrolidinyloxy, tetrahydrofuryloxy, thiolanyloxy, piperidyloxy);
(68) a 8- to 12-membered fused non-aromatic heterocyclyloxy group (e.g., dihydrobenzofuranyloxy);
(69) a carboxy group;
(70) a $C_{1-6}$ alkoxy-carbonyl group;
(71) a $C_{2-6}$ alkenyloxy-carbonyl group (e.g., vinyloxycarbonyl, propenyloxycarbonyl, butenyloxycarbonyl, pentenyloxycarbonyl, hexenyloxycarbonyl);
(72) a $C_{2-6}$ alkynyloxy-carbonyl group (e.g., ethynyloxycarbonyl, propynyloxycarbonyl, butynyloxycarbonyl, pentynyloxycarbonyl, hexynyloxycarbonyl);
(73) a $C_{3-8}$ cycloalkyloxy-carbonyl group (e.g., cyclopropyloxycarbonyl, cyclobutyloxycarbonyl, cyclopentyloxycarbonyl, cyclohexyloxycarbonyl);
(74) a $C_{3-8}$ cycloalkenyloxy-carbonyl group (e.g., cyclopropenyloxycarbonyl, cyclobutenyloxycarbonyl, cyclopentenyloxycarbonyl, cyclohexenyloxycarbonyl);
(75) a $C_{6-14}$ aryloxy-carbonyl group (e.g., phenoxycarbonyl, 1-naphthyloxycarbonyl, 2-naphthyloxycarbonyl);
(76) a $C_{3-8}$ cycloalkyl-$C_{1-6}$ alkoxy-carbonyl group (e.g., cyclopropylmethyloxycarbonyl, cyclopropylethyloxycarbonyl, cyclobutylmethyloxycarbonyl, cyclopentylmethyloxycarbonyl, cyclohexylmethyloxycarbonyl, cyclohexylethyloxycarbonyl);
(77) a $C_{3-8}$ cycloalkenyl-$C_{1-6}$ alkoxy-carbonyl group (e.g., cyclopentenylmethyloxycarbonyl, cyclohexenylmethyloxycarbonyl, cyclohexenylethyloxycarbonyl, cyclohexenylpropyloxycarbonyl);
(78) a $C_{7-14}$ aralkyloxy-carbonyl group (e.g., benzyloxycarbonyl, phenethyloxycarbonyl);
(79) a mono-$C_{1-6}$ alkyl-thiocarbamoyl group (e.g., methylthiocarbamoyl, ethylthiocarbamoyl, propylthiocarbamoyl);
(80) a di-$C_{1-6}$ alkyl-thiocarbamoyl group (e.g., dimethylthiocarbamoyl, diethylthiocarbamoyl, dipropylthiocarbamoyl);
(81) a $C_{1-6}$ alkyl-carbonyloxy group (e.g., acetyloxy, propanoyloxy, butanoyloxy, 2-methylpropanoyloxy);
(82) an imino group optionally substituted by a hydroxy group; and
(83) a $C_{1-6}$ alkylenedioxy group (e.g., methylenedioxy, ethylenedioxy).

The $C_{2-10}$ alkenyl group and $C_{1-6}$ alkyl-carbonyl group optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-10}$ cycloalkyl group, $C_{3-10}$ cycloalkenyl group and non-aromatic heterocyclic group optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

The $C_{6-14}$ aryl group, $C_{8-14}$ aralkyl group, $C_{8-13}$ aryl alkenyl group and aromatic heterocyclic group optionally have 1 to 5 (preferably 1 to 3) substituents at substitutable position(s). Examples of the substituent include substituents selected from the above-mentioned Substituent Group B excluding an oxo group. When the number of the substituents is plural, the respective substituents may be the same or different.

Examples of the "optionally substituted sulfanyl group" exemplified as the "substituent" for $R^1$ or $R^2$ include a sulfanyl group optionally substituted by a substituent selected from a $C_{1-10}$ alkyl group, a $C_{2-10}$ alkenyl group; a $C_{3-10}$ cycloalkyl group, a $C_{3-10}$ cycloalkenyl group, a $C_{6-14}$ aryl group, a $C_{7-14}$ aralkyl group, a $C_{8-13}$ aryl alkenyl group, a $C_{1-6}$ alkyl-carbonyl group, a heterocyclic group (e.g., an aromatic heterocyclic group, a non-aromatic heterocyclic group) and the like, each of which is optionally substituted.

The $C_{1-10}$ alkyl group, $C_{2-10}$ alkenyl group and $C_{1-6}$ alkyl-carbonyl group optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-10}$ cycloalkyl group, $C_{3-10}$ cycloalkenyl group and non-aromatic heterocyclic group optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

The $C_{6-14}$ aryl group, $C_{7-14}$ aralkyl group, $C_{8-13}$ aryl alkenyl group and aromatic heterocyclic group optionally have 1 to 5 (preferably 1 to 3) substituents at substitutable position(s). Examples of the substituent include substituents selected from the above-mentioned Substituent Group B excluding an oxo group. When the number of the substituents is plural, the respective substituents may be the same or different.

Examples of the "optionally substituted amino group" exemplified as the "substituent" for $R^1$ or $R^2$ include an amino group optionally mono- or di-substituted by substituent(s) selected from a $C_{1-10}$ alkyl group, a $C_{2-10}$ alkenyl group, a $C_{3-10}$ cycloalkyl group, a $C_{3-10}$ cycloalkenyl group, a $C_{6-14}$ aryl group, a $C_{7-14}$ aralkyl group, a $C_{8-13}$ aryl alkenyl group, a heterocyclic group (e.g., an aromatic heterocyclic group, a non-aromatic heterocyclic group) and the like, each of which is optionally substituted; and an acyl group. When the amino is di-substituted, the two substituents in combination optionally form an optionally substituted heterocyclic group.

The $C_{1-10}$ alkyl group and $C_{2-10}$ alkenyl group optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-10}$ cycloalkyl group, $C_{3-10}$ cycloalkenyl group and non-aromatic heterocyclic group optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

The $C_{6-14}$ aryl group, $C_{7-14}$ aralkyl group, $C_{8-13}$ aryl alkenyl group and aromatic heterocyclic group optionally have 1 to 5 (preferably 1 to 3) substituents at substitutable position(s). Examples of the substituent include substituents selected from the above-mentioned Substituent Group B excluding an oxo group. When the number of the substituents is plural, the respective substituents may be the same or different.

Examples of the "acyl group" exemplified as the substituent for the "amino group" include those similar to the below-mentioned "acyl group" exemplified as the "substituent" for $R^1$ or $R^2$.

Examples of the "acyl group" exemplified as the "substituent" for $R^1$ or $R^2$ include a group represented by the formula: —$COR^A$, —CO—$OR^A$, —$SO_3R^A$, —$S(O)_2R^A$, —$SOR^A$, —CO—$NR^{A'}R^{B'}$, —CS—$NR^{A'}R^{B'}$ or —$S(O)_2NR^{A'}R^{B'}$ wherein $R^A$ is a hydrogen atom, an optionally substituted hydrocarbon group or an optionally substituted heterocyclic group, and $R^{A'}$ and $R^{B'}$ are the same or different and each is a hydrogen atom, an optionally substituted hydrocarbon group or an optionally substituted heterocyclic group, or $R^{A'}$ and $R^{B'}$ optionally form, together with the adjacent nitrogen atom, an optionally substituted nitrogen-containing heterocycle, and the like.

Examples of the "hydrocarbon group" of the "optionally substituted hydrocarbon group for $R^A$, $R^{A'}$ or $R^{B'}$ include a $C_{1-10}$ alkyl group, a $C_{2-10}$ alkenyl group, a $C_{2-10}$ alkynyl group, a $C_{3-10}$ cycloalkyl group, a $C_{3-10}$ cycloalkenyl group, a $C_{4-10}$ cycloalkadienyl group, a $C_{6-14}$ aryl group, a $C_{7-14}$ aralkyl group, a $C_{8-13}$ aryl alkenyl group and the like.

The above-mentioned $C_{1-10}$ alkyl group, $C_{2-10}$ alkenyl group and $C_{2-10}$ alkynyl group exemplified as the "hydrocarbon group" optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The above-mentioned $C_{3-10}$ cycloalkyl group, $C_{3-10}$ cycloalkenyl group and $C_{4-10}$ cycloalkadienyl group exemplified as the "hydrocarbon group" optionally have 1 to 5 (preferably 1 to 3) substituents at substitutable position(s). Examples of the substituent include substituents selected from the above-mentioned Substituent Group B. When the number of the substituents is plural, the respective substituents may be the same or different.

The above-mentioned $C_{6-14}$ aryl group, $C_{7-14}$ aralkyl group and $C_{8-13}$ aryl alkenyl group exemplified as the "hydrocarbon group" optionally have 1 to 5 (preferably 1 to 3) substituents at substitutable position(s). Examples of the substituent include substituents selected from the above-mentioned Substituent Group B excluding an oxo group. When the number of the substituents is plural, the respective substituents may be the same or different.

The "heterocyclic group" of the "optionally substituted heterocyclic group" for $R^A$, $R^{A'}$ or $R^{B'}$ optionally has 1 to 5 (preferably 1 to 3) substituents at substitutable position(s). Examples of the substituent for the aromatic heterocyclic group include substituents selected from the above-mentioned Substituent Group B excluding an oxo group, and examples of the substituent for the non-aromatic heterocyclic group include substituents selected from the above-mentioned Substituent Group B. When the number of the substituents is plural, the respective substituents may be the same or different.

Examples of the "nitrogen-containing heterocycle" of the "optionally substituted nitrogen-containing heterocycle" formed by $R^{A'}$ and $R^{B'}$ together with the adjacent nitrogen atom include a 5- to 7-membered nitrogen-containing heterocycle optionally containing, as a ring-constituting atom besides carbon atom, at least one nitrogen atom, and additional 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine and the like.

The nitrogen-containing heterocycle optionally has 1 to 5 (preferably 1 to 3) substituents at substitutable position(s). Examples of the substituent include substituents selected from the above-mentioned Substituent Group B. When the number of the substituents is plural, the respective substituents may be the same or different.

Preferable examples of the "optionally substituted acyl" include (1) a formyl group;
(2) a carboxy group;
(3) a $C_{1-6}$ alkyl-carbonyl group (e.g., acetyl) optionally substituted by 1 to 3 halogen atoms;
(4) a $C_{1-6}$ alkoxy-carbonyl group (e.g., methoxycarbonyl, ethoxycarbonyl, propoxycarbonyl, tert-butoxycarbonyl) optionally substituted by 1 to 3 halogen atoms;
(5) a $C_{3-10}$ cycloalkyl-carbonyl group (e.g., cyclopropylcarbonyl, cyclopentylcarbonyl, cyclohexylcarbonyl);
(6) a $C_{6-14}$ aryl-carbonyl group (e.g., benzoyl, 1-naphthoyl, 2-naphthoyl) optionally substituted by 1 to 3 halogen atoms;

(7) a carbamoyl group optionally mono- or di-substituted by substituent(s) selected from
  (a) a $C_{1-6}$ alkyl group optionally substituted by 1 to 3 substituents selected from a halogen atom, a $C_{1-6}$ alkoxy group, a $C_{1-6}$ alkoxy-carbonyl group and a carboxy group, and
  (b) an amino group optionally mono or di-substituted by $C_{1-6}$ alkoxy-carbonyl group(s);
(8) a $C_{1-6}$ alkylsulfonyl group (e.g., methylsulfonyl, ethylsulfonyl, isopropylsulfonyl) optionally substituted by 1 to 3 halogen atoms;
(9) a $C_{6-14}$ aryl sulfonyl group (e.g., benzenesulfonyl);
(10) a sulfamoyl group;
(11) a thiocarbamoyl group;
(12) an aromatic heterocyclylcarbonyl group (e.g., furylcarbonyl, thienylcarbonyl) optionally substituted by 1 to 3 substituents selected from a $C_{1-6}$ alkyl group optionally substituted by 1 to 3 halogen atoms;
(13) a non-aromatic heterocyclylcarbonyl group (e.g., tetrahydrofurylcarbonyl, pyrrolidinocarbonyl) optionally substituted by 1 to 3 substituents selected from a $C_{1-6}$ alkyl group optionally substituted by 1 to 3 halogen atoms; and the like.

$R^1$ is preferably an optionally substituted aromatic ring group, $-OR^8$, $-NHR^8$, $-NR^8R^{8'}$ or $-SR^8$ wherein $R^8$ and $R^{8'}$ are each independently an optionally substituted $C_{1-10}$ alkyl group, an optionally substituted $C_{2-10}$ alkenyl group, an optionally substituted $C_{2-10}$ alkynyl group, an optionally substituted $C_{3-10}$ cycloalkyl group, an optionally substituted $C_{3-10}$ cycloalkenyl group, an optionally substituted $C_{4-10}$ cycloalkadienyl group, an optionally substituted $C_{6-14}$ aryl group, an optionally substituted $C_{8-14}$ aralkyl group or an optionally substituted $C_{8-13}$ aryl alkenyl group.

The "aromatic ring group" of the "optionally substituted aromatic ring group" optionally has 1 to 5 (preferably 1 to 3) substituents at substitutable position(s). Examples of the substituent include substituents selected from the above-mentioned Substituent Group B excluding an oxo group. When the number of the substituents is plural, the respective substituents may be the same or different.

The $C_{1-10}$ alkyl group, $C_{2-10}$ alkenyl group and $C_{2-10}$ alkynyl group of the "optionally substituted $C_{1-10}$ alkyl group", "optionally substituted $C_{2-10}$ alkenyl group" and "optionally substituted $C_{2-10}$ alkynyl group" for $R^8$ or $R^{8'}$ each optionally have 1 to 5 (preferably 1 to 3) substituents at substitutable position(s). Examples of the substituent include substituents selected from the above-mentioned Substituent Group A. When the number of the substituents is plural, the respective substituents may be the same or different.

The $C_{3-10}$ cycloalkyl group, $C_{3-10}$ cycloalkenyl group and $C_{4-10}$ cycloalkadienyl group of the "optionally substituted $C_{3-10}$ cycloalkyl group", "optionally substituted $C_{3-10}$ cycloalkenyl group" and "optionally substituted $C_{4-10}$ cycloalkadienyl group" for $R^8$ or $R^{8'}$ each optionally have 1 to 5 (preferably 1 to 3) substituents at substitutable position (s). Examples of the substituent include substituents selected from the above-mentioned Substituent Group B. When the number of the substituents is plural, the respective substituents may be the same or different.

The $C_{6-14}$ aryl group, $C_{8-14}$ aralkyl group and $C_{8-13}$ aryl alkenyl group of the "optionally substituted $C_{6-14}$ aryl group", "optionally substituted $C_{8-14}$ aralkyl group" and "optionally substituted $C_{8-13}$ aryl alkenyl group" for $R^8$ or $R^{8'}$ each optionally have 1 to 5 (preferably 1 to 3) substituents at substitutable position(s). Examples of the substituent include substituents selected from the above-mentioned Substituent Group B excluding an oxo group. When the number of the substituents is plural, the respective substituents may be the same or different.

$R^1$ is
more preferably an optionally substituted $C_{6-14}$ aryl group, $-OR^8$ or $-SR^8$ wherein $R^8$ is as defined above,
further more preferably an optionally substituted $C_{6-14}$ aryl group, $-OR^8$ or $-SR^8$ wherein $R^8$ is an optionally substituted $C_{1-10}$ alkyl group (preferably a $C_{1-6}$ alkyl group), an optionally substituted $C_{6-14}$ aryl group or an optionally substituted $C_{8-14}$ aralkyl group,
still more preferably
(i) a $C_{6-14}$ aryl group (e.g., phenyl),
(ii) $-OR^8$ wherein $R^8$ is a $C_{1-10}$ alkyl group (preferably a $C_{1-6}$ alkyl group (e.g., methyl)) or a $C_{6-14}$ aryl group (e.g., phenyl)), or
(iii) $-SR^8$ wherein $R^8$ is a $C_{6-14}$ aryl group (e.g., phenyl).

In another embodiment, $R^1$ is more preferably an optionally substituted $C_{6-14}$ aryl group, or $-OR^8$ wherein $R^8$ is as defined above,
further more preferably an optionally substituted $C_{6-14}$ aryl group, or $-OR^8$ wherein $R^8$ is an optionally substituted $C_{1-10}$ alkyl group (preferably a $C_{1-6}$ alkyl group), an optionally substituted $C_{6-14}$ aryl group or an optionally substituted $C_{8-14}$ aralkyl group,
still more preferably $-OR^8$ wherein $R^8$ is an optionally substituted $C_{1-10}$ alkyl group (preferably a $C_{1-6}$ alkyl group),
still more preferably a $C_{1-10}$ alkoxy group (preferably a $C_{1-6}$ alkoxy group),
still more preferably a $C_{1-6}$ alkoxy group (e.g., methoxy), particularly preferably methoxy.

$R^2$ is preferably (1) a hydrogen atom, (2) an optionally substituted $C_{1-10}$ alkyl group, (3) an optionally substituted $C_{2-10}$ alkenyl group, (4) an optionally substituted $C_{2-10}$ alkynyl group, or (5) an optionally substituted $C_{3-10}$ cycloalkyl group.

$R^2$ is
more preferably a hydrogen atom, or an optionally substituted $C_{1-10}$ alkyl group (preferably a. $C_{1-6}$ alkyl group),
further more preferably a hydrogen atom or a $C_{1-10}$ alkyl group (preferably a $C_{1-6}$ alkyl group),
still more preferably a hydrogen atom or a $C_{1-6}$ alkyl group (e.g., methyl),
still more preferably a hydrogen atom or methyl, particularly preferably a hydrogen atom.

As preferable combination,
$R^1$ is an optionally substituted aromatic ring group, $-OR^8$, $-NHR^8$, $-NR^8R^{8'}$ or $-SR^8$ wherein $R^8$ and $R^{8'}$ are each independently an optionally substituted $C_{1-10}$ alkyl group, an optionally substituted $C_{2-10}$ alkenyl group, an optionally substituted $C_{2-10}$ alkynyl group, an optionally substituted $C_{3-10}$ cycloalkyl group, an optionally substituted $C_{3-10}$ cycloalkenyl group, an optionally substituted $C_{4-10}$ cycloalkadienyl group, an optionally substituted $C_{6-14}$ aryl group, an optionally substituted $C_{8-14}$ aralkyl group or an optionally substituted $C_{8-13}$ aryl alkenyl group, and
$R^2$ is (1) a hydrogen atom, (2) an optionally substituted $C_{1-10}$ alkyl group, (3) an optionally substituted $C_{2-10}$ alkenyl group, (4) an optionally substituted $C_{2-10}$ alkynyl group, or (5) an optionally substituted $C_{3-10}$ cycloalkyl group.

As more preferable combination,
$R^1$ is an optionally substituted $C_{6-14}$ aryl group, $-OR^8$ or $-SR^8$ wherein $R^8$ is as defined above, and
$R^2$ is a hydrogen atom or an optionally substituted $C_{1-10}$ alkyl group (preferably a $C_{1-6}$ alkyl group).

As further more preferable combination,
$R^1$ is an optionally substituted $C_{6-14}$ aryl group, —$OR^8$ or —$SR^8$ wherein $R^8$ is an optionally substituted $C_{1-10}$ alkyl group (preferably a $C_{1-6}$ alkyl group), an optionally substituted $C_{6-14}$ aryl group or an optionally substituted $C_{8-14}$ aralkyl group, and $R^2$ is a hydrogen atom or a $C_{1-10}$ alkyl group (preferably a $C_{1-6}$ alkyl group).

As still more preferable combination,
$R^1$ is
(i) a $C_{6-14}$ aryl group (e.g., phenyl),
(ii) —$OR^8$ wherein $R^8$ is a $C_{1-10}$ alkyl group (preferably a $C_{1-6}$ alkyl group (e.g., methyl)) or a $C_{6-14}$ aryl group (e.g., phenyl)), or
(iii) —$SR^8$ wherein $R^8$ is a $C_{6-14}$ aryl group (e.g., phenyl), and $R^2$ is a hydrogen atom or a $C_{1-6}$ alkyl group (e.g., methyl).

Ring A is an optionally substituted aromatic ring.

The "aromatic ring" of the "optionally substituted aromatic ring" for Ring A optionally has 1 to 5 (preferably 1 to 3) substituents at substitutable position(s). Examples of the substituent include substituents selected from the above-mentioned Substituent Group B excluding an oxo group. When the number of the substituents is plural, the respective substituents may be the same or different.

Ring A is
preferably an optionally substituted $C_{6-14}$ aromatic hydrocarbon, more preferably an optionally substituted benzene, further more preferably benzene substituted by cyclic group(s) (preferably a 5- or 6-membered monocyclic aromatic heterocyclic group(s) (preferably pyrazolyl)), and optionally further substituted,
still more preferably benzene substituted by 5- or 6-membered monocyclic aromatic heterocyclic group(s) (preferably pyrazolyl), and optionally further substituted by 1 to 5 (preferably 1 to 3) halogen atoms (preferably a fluorine atom), still more preferably benzene substituted by one 5- or 6-membered monocyclic aromatic heterocyclic group (preferably pyrazolyl), and further optionally substituted by 1 to 5 (preferably 1 to 3) halogen atoms (preferably a fluorine atom), still more preferably benzene substituted by one 5- or 6-membered monocyclic aromatic heterocyclic group (preferably pyrazolyl) and one halogen atom (preferably a fluorine atom), particularly preferably benzene substituted by one fluorine atom and one pyrazolyl (particularly 4-(pyrazol-1-yl)-2-fluorobenzene).

$R^{3a}$, $R^{4a}$, $R^{5a}$ and $R^{6a}$ are each independently an optionally substituted hydrocarbon group.

$R^{3b}$, $R^{4b}$, $R^{5b}$ and $R^{6b}$ are each independently an optionally substituted hydrocarbon group.

$R^3$, $R^4$, $R^5$ and $R^6$ are each independently an optionally substituted hydrocarbon group.

Examples of the "optionally substituted hydrocarbon group" for $R^{3a}$, $R^{4a}$, $R^{5a}$, $R^{6a}$, $R^{3b}$, $R^{4b}$, $R^{5b}$, $R^{6b}$, $R^3$, $R^4$, $R^5$ or $R^6$ include those similar to the "optionally substituted hydrocarbon group" exemplified as the "substituent" for $R^1$ or $R^2$.

$R^{3a}$, $R^{4a}$, $R^{5a}$ and $R^{6a}$ are
preferably each independently an optionally substituted $C_{1-10}$ alkyl group (preferably a $C_{1-6}$ alkyl group),
more preferably each independently a $C_{1-10}$ alkyl group (preferably a $C_{1-6}$ alkyl group),
still more preferably each independently a $C_{1-6}$ alkyl group (e.g., methyl),
particularly preferably all methyl.

$R^{3b}$, $R^{4b}$, $R^{5b}$ and $R^{6b}$ are
preferably each independently an optionally substituted $C_{1-10}$ alkyl group (preferably a $C_{1-6}$ alkyl group),
more preferably each independently a $C_{1-10}$ alkyl group (preferably a $C_{1-6}$ alkyl group),
still more preferably each independently a $C_{1-6}$ alkyl group (e.g., methyl),
particularly preferably all methyl.

$R^3$, $R^4$, $R^5$ and $R^6$ are
preferably each independently an optionally substituted $C_{1-10}$ alkyl group (preferably a $C_{1-6}$ alkyl group),
more preferably each independently a $C_{1-10}$ alkyl group (preferably a $C_{1-6}$ alkyl group),
still more preferably each independently a $C_{1-6}$ alkyl group (e.g., methyl),
particularly preferably all methyl.

$R^7$ is an optionally substituted hydrocarbon group or an optionally substituted heterocyclic group.

Examples of the "optionally substituted hydrocarbon group" for $R^7$ include those similar to the "optionally substituted hydrocarbon group" exemplified as the "substituent" for $R^1$ or $R^2$.

Examples of the "optionally substituted heterocyclic group" for $R^7$ include those similar to the "optionally substituted heterocyclic group" exemplified as the "substituent" for $R^1$ or $R^2$.

$R^7$ is
preferably an optionally substituted hydrocarbon group, more preferably an optionally substituted $C_{6-14}$ aryl group, still more preferably an optionally substituted phenyl, particularly preferably phenyl.

$R^{1a}$ is —$OR^9$ wherein $R^9$ is a substituent (excluding an ethenyl group and a benzyl group).

Examples of the "substituent" for $R^9$ include those similar to the "substituent" for $R^1$ or $R^2$. An ethenyl group and a benzyl group are excluded from $R^9$.

$R^{1a}$ is
preferably —$OR^9$ wherein $R^9$ is an optionally substituted hydrocarbon group (excluding an ethenyl group and a benzyl group),
more preferably —$OR^9$ wherein $R^9$ is an optionally substituted $C_{1-10}$ alkyl group (preferably a $C_{1-6}$ alkyl group), an optionally substituted $C_{6-14}$ aryl group or an optionally substituted $C_{8-14}$ aralkyl group),
further more preferably —$OR^9$ wherein $R^9$ is an optionally substituted $C_{1-10}$ alkyl group (preferably a $C_{1-6}$ alkyl group),
still more preferably a $C_{1-10}$ alkoxy group (preferably a $C_{1-6}$ alkoxy group),
still more preferably a $C_{1-6}$ alkoxy group (e.g., methoxy), particularly preferably methoxy.

$R^{2a}$ is a hydrogen atom or a substituent.

Examples of the "substituent" for $R^{2a}$ include those similar to the "substituent" for $R^1$ or $R^2$.

$R^{2a}$ is preferably (1) a hydrogen atom, (2) an optionally substituted $C_{1-10}$ alkyl group, (3) an optionally substituted $C_{2-10}$ alkenyl group, (4) an optionally substituted $C_{2-10}$ alkynyl group, or (5) an optionally substituted $C_{3-10}$ cycloalkyl group.

$R^{2a}$ is
more preferably a hydrogen atom, or an optionally substituted $C_{1-10}$ alkyl group (preferably a $C_{1-6}$ alkyl group),
further more preferably a hydrogen atom or a $C_{1-10}$ alkyl group (preferably a $C_{1-6}$ alkyl group),
still more preferably a hydrogen atom or a $C_{1-6}$ alkyl group (e.g., methyl), still more preferably a hydrogen atom or methyl, particularly preferably a hydrogen atom.

Ring Aa is an optionally substituted aromatic ring.

Examples of the "optionally substituted aromatic ring" for Ring Aa include those similar to the "optionally substituted aromatic ring" for Ring A.

Ring Aa is
preferably an optionally substituted $C_{6-14}$ aromatic-hydrocarbon, more preferably an optionally substituted benzene, further more preferably benzene substituted by cyclic group(s) (preferably a 5- or 6-membered monocyclic aromatic heterocyclic group(s) (preferably pyrazolyl)), and optionally further substituted,
still more preferably benzene substituted by 5- or 6-membered monocyclic aromatic heterocyclic group(s) (preferably pyrazolyl), and optionally further substituted by 1 to 5 (preferably 1 to 3) halogen atoms (preferably a fluorine atom),
still more preferably benzene substituted by one 5- or 6-membered monocyclic aromatic heterocyclic group (preferably pyrazolyl), and further substituted by 1 to 5 (preferably 1 to 3) halogen atoms (preferably a fluorine atom),
still more preferably benzene substituted by one 5- or 6-membered monocyclic aromatic heterocyclic group (preferably pyrazolyl) and one halogen atom (preferably a fluorine atom), particularly preferably benzene substituted by one fluorine atom and one pyrazolyl (particularly 4-(pyrazol-1-yl)-2-fluorobenzene).

Preferable examples of compound (I) include
a compound wherein
$R^1$ is
(i) a $C_{6-14}$ aryl group (e.g., phenyl),
(ii) —$OR^8$ wherein $R^8$ is a $C_{1-10}$ alkyl group (preferably a $C_{1-6}$ alkyl group (e.g., methyl)) or a $C_{6-14}$ aryl group (e.g., phenyl)), or
(iii) —$SR^8$ wherein $R^8$ is a $C_{6-14}$ aryl group (e.g., phenyl), $R^2$ is a hydrogen atom or a $C_{1-6}$ alkyl group (e.g., methyl), Ring A is benzene substituted by 5- or 6-membered monocyclic aromatic heterocyclic group(s) (preferably pyrazolyl), and optionally further optionally substituted by 1 to 5 (preferably 1 to 3) halogen atoms (preferably a fluorine atom), and
$R^7$ is phenyl,
particularly 1-[2-fluoro-4-(1H-pyrazol-1-yl)phenyl]-5-methoxy-3-(1-phenyl-1H-pyrazol-5-yl)pyridazin-4(1H)-one (compound A).

Each step in the production method of the present invention is explained in the following.

The pyridazinone compound of the present invention is produced according to the following steps.

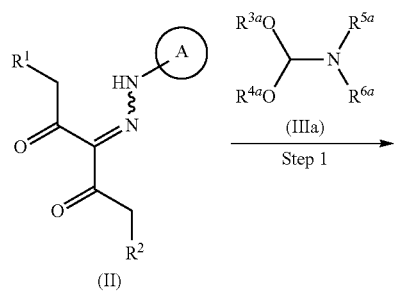

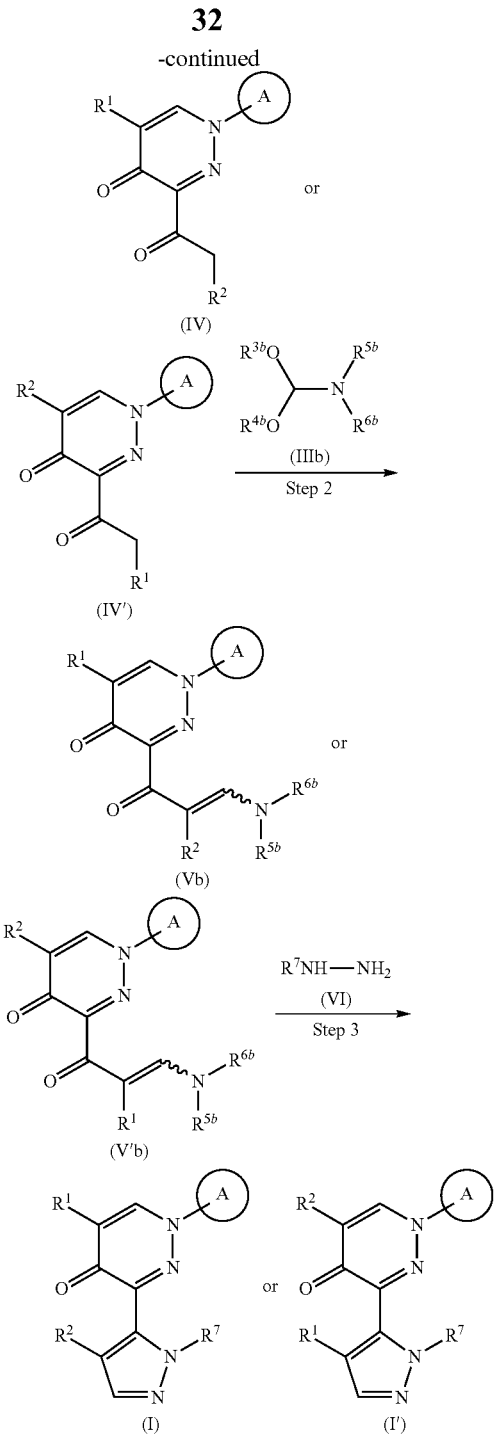

wherein each symbol is as defined above.

Step 1

In this step, compound (IV) or compound (IV') or a mixture thereof is produced by reacting compound (II) with compound (IIIa).

This reaction can be carried out according to the method described in Journal of Heterocyclic Chemistry, 1981, 18, 333-334 or a method analogous thereto.

Examples of the compound (IIIa) include N,N-dimethylformamide dimethyl acetal, N,N-dimethylformamide diethyl acetal, N,N-dimethylformamide diisopropyl acetal, N,N-dimethylformamide dipropyl acetal, N,N-diethylformamide dimethyl acetal and the like.

The amount of compound (IIIa) to be used is generally 1 to 100 mol, preferably 1 to 50 mol, per 1 mol of compound (II).

The reaction is carried out without solvent or in a solvent inert to the reaction. The solvent is not particularly limited as long as the reaction proceeds. Preferable examples thereof include alcohols (e.g., methanol, ethanol, propanol, butanol and the like), hydrocarbons (e.g., benzene, toluene, xylene and the like), halogenated hydrocarbons (e.g., chloroform, dichloromethane and the like), ethers (e.g., diethyl ether, diisopropyl ether, tetrahydrofuran and the like), esters (e.g., ethyl acetate and the like), amides (e.g., N,N-dimethylformamide, N,N-dimethylacetamide and the like), nitriles (e.g., acetonitrile and the like), sulfoxides (e.g., dimethylsulfoxide and the like), water and mixed solvents thereof.

The amount of the solvent to be used is generally 1 to 100-fold weights, preferably 1 to 80-fold weights, relative to compound (II).

The reaction is generally carried out at 0 to 150° C., preferably 0 to 80° C., more preferably 0 to 70° C., still more preferably 0 to 65° C.

While the reaction time varies depending on the kind of compound (II) and compound (IIIa), and the reaction temperature, it is generally 0.1 to 24 hr, preferably 0.5 to hr.

While the product can be used for the next reaction as the reaction mixture or as a crude product, or can also be isolated according to a conventional method from the reaction mixture, and can also be purified according to a separation means such as recrystallization, distillation, chromatography, HPLC and the like, it is preferably directly used for the next reaction as a crude product from the aspect of easiness.

When a mixture of compound (IV) and compound (IV') is obtained, while compound (IV) and compound (IV') can be isolated according to a separation means such as recrystallization, distillation, chromatography, HPLC and the like, the mixture is preferably directly used for the next reaction from the aspect of easiness.

Since $R^1$ is different from $R^2$ in the present invention, compound (IV) or compound (IV') or a mixture thereof is obtained in this step. The reaction proceeds selectively depending on the combination of $R^1$ and $R^2$. For example, when $R^1$ is an optionally substituted aromatic ring group, —$OR^8$, —$NHR^8$, —$NR^8R^{8'}$ or —$SR^8$ wherein each symbol is as defined above, and
$R^2$ is (1) a hydrogen atom, (2) an optionally substituted $C_{1-10}$ alkyl group, (3) an optionally substituted $C_{2-10}$ alkenyl group, (4) an optionally substituted $C_{2-10}$ alkynyl group, or (5) an optionally substituted $C_{3-10}$ cycloalkyl group, preferably when
$R^1$ is optionally substituted $C_{6-14}$ aryl group, —$OR^8$ or —$SR^8$ wherein $R^8$ is as defined above
[preferably an optionally substituted $C_{6-14}$ aryl group, —$OR^8$ or —$SR^8$ wherein $R^8$ is an optionally substituted $C_{1-10}$ alkyl group (preferably a $C_{1-6}$ alkyl group), an optionally substituted $C_{6-14}$ aryl group or an optionally substituted $C_{6-14}$ aralkyl group, more preferably
(i) a $C_{6-14}$ aryl group (e.g., phenyl),
(ii) —$OR^8$ wherein $R^8$ is a $C_{1-10}$ alkyl group (preferably a $C_{1-6}$ alkyl group (e.g., methyl)) or a $C_{6-14}$ aryl group (e.g., phenyl)), or
(iii) —$SR^8$ wherein $R^8$ is $C_{6-14}$ aryl group (e.g., phenyl), further more preferably a $C_{1-10}$ alkoxy group (preferably $C_{1-6}$ alkoxy group),
still more preferably a $C_{1-6}$ alkoxy group (e.g., methoxy), particularly preferably methoxy], and $R^2$ is a hydrogen atom, or an optionally substituted $C_{1-10}$ alkyl group (preferably a $C_{1-6}$ alkyl group)
[preferably a hydrogen atom or a $C_{1-10}$ alkyl group (preferably a $C_{1-6}$ alkyl group),
more preferably a hydrogen atom or a $C_{1-6}$ alkyl group (e.g., methyl),
still more preferably a hydrogen atom or methyl,
particularly preferably a hydrogen atom],
compound (IV) is preferentially obtained.

Step 2

In this step, compound (Vb) or compound (V'b) or a mixture thereof is produced by reacting compound (IV) or compound (IV') or a mixture thereof with compound (IIIb).

This step is carried out according to a method similar to that in Step 1.

Examples of the compound (IIIb) include N,N-dimethylformamide dimethyl acetal, N,N-dimethylformamide diethyl acetal, N,N-dimethylformamide diisopropyl acetal, N,N-dimethylformamide dipropyl acetal, N,N-diethylformamide dimethyl acetal and the like.

The amount of compound (IIIb) to be used is generally 1 to 100 mol, preferably 1 to 50 mol, per 1 mol of compound (IV) or compound (IV') or a mixture thereof.

The reaction is carried out without solvent or in a solvent inert to the reaction. The solvent is not particularly limited as long as the reaction proceeds. Preferable examples thereof include alcohols (e.g., methanol, ethanol, propanol, butanol and the like), hydrocarbons (e.g., benzene, toluene, xylene and the like), halogenated hydrocarbons (e.g., chloroform, dichloromethane and the like), ethers (e.g., diethyl ether, diisopropyl ether, tetrahydrofuran and the like), esters (e.g., ethyl acetate and the like), amides (e.g., N,N-dimethylformamide, N,N-dimethylacetamide and the like), nitriles (e.g., acetonitrile and the like), sulfoxides (e.g., dimethylsulfoxide and the like), water and mixed solvents thereof.

The amount of the solvent to be used is generally 1 to 100-fold weights, preferably 1 to 80-fold weights, relative to compound (IV) or compound (IV') or a mixture thereof.

The reaction is generally carried out at 0 to 150° C., preferably 0 to 80° C., more preferably 0 to 70° C., still more preferably 0 to 65° C.

While the reaction time varies depending on the kind of compound (IV) or compound (IV') and compound (IIIb), and the reaction temperature, it is generally 0.1 to 24 hr, preferably 0.5 to 10 hr.

While the product can be used for the next reaction as the reaction mixture or as a crude product, or can also be isolated according to a conventional method from the reaction mixture, and can also be purified according to a separation means such as recrystallization, distillation, chromatography, HPLC and the like, it is preferably directly used for the next reaction as a crude product from the aspect of easiness.

When a mixture of compound (Vb) and compound (V'b) is obtained, while compound (Vb) and compound (V'b) can be isolated according to a separation means such as recrystallization, distillation, chromatography, HPLC and the like, the mixture is preferably directly used for the next reaction from the aspect of easiness.

Alternatively, compound (V) or compound (V') or a mixture thereof can also be produced by reacting compound (II) with compound (III) (Step 1+2).

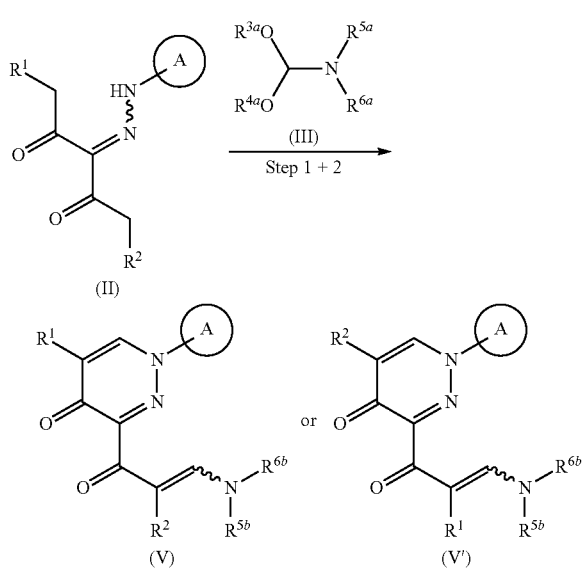

wherein each symbol is as defined above.

This reaction can be carried out according to the method described in Journal of Heterocyclic Chemistry, 1981, 18, 333-334 or a method analogous thereto.

Examples of the compound (III) include N,N-dimethylformamide dimethyl acetal, N,N-dimethylformamide diethyl acetal, N,N-dimethylformamide diisopropyl acetal, N,N-dimethylformamide dipropyl acetal, N,N-diethylformamide dimethyl acetal and the like.

The amount of the compound (III) to be used is generally 1 to 200 mol, preferably 1 to 100 mol, per 1 mol of compound (II).

The reaction is carried out without solvent or in a solvent inert to the reaction. The solvent is not particularly limited as long as the reaction proceeds. Preferable examples thereof include alcohols (e.g., methanol, ethanol, propanol, butanol and the like), hydrocarbons (e.g., benzene, toluene, xylene and the like), halogenated hydrocarbons (e.g., chloroform, dichloromethane and the like), ethers (e.g., diethyl ether, diisopropyl ether, tetrahydrofuran and the like), esters (e.g., ethyl acetate and the like), amides (e.g., N,N-dimethylformamide, N,N-dimethylacetamide and the like), nitriles (e.g., acetonitrile and the like), sulfoxides (e.g., dimethylsulfoxide and the like), water and mixed solvents thereof.

The amount of the solvent to be used is generally 1 to 100-fold weights, preferably 1 to 80-fold weights, relative to compound (II).

The reaction is generally carried out at 0 to 150° C., preferably 0 to 80° C., more preferably 0 to 70° C., still more preferably 0 to 65° C.

While the reaction time varies depending on the kind of compound (II) and compound (III), and the reaction temperature, it is generally 0.1 to 24 hr, preferably 0.5 to 10 hr.

While the product can be used for the next reaction as the reaction mixture or as a crude product, or can also be isolated according to a conventional method from the reaction mixture, and can also be purified according to a separation means such as recrystallization, distillation, chromatography, HPLC and the like, it is preferably directly used for the next reaction as a crude product from the aspect of easiness.

When a mixture of compound (V) and compound (V') is obtained, while compound (V) and compound (V') can be isolated according to a separation means such as recrystallization, distillation, chromatography, HPLC and the like, the mixture is preferably directly used for the next reaction from the aspect of easiness.

Step 3

In this step, compound (I) or compound (I') or a mixture thereof is produced by reacting compound (Vb) or compound (V'b) or a mixture thereof (or compound (V) or compound (V') or a mixture thereof) with compound (VI). Since compound (IV) is preferentially obtained by selecting the combination of $R^1$ and $R^2$ in Step 1, compound (I) is preferentially obtained from compound (IV) via Step 2 and Step 3.

This reaction can be carried out according to the method described in Journal of Heterocyclic Chemistry, 1981, 18, 333-334 or a method analogous thereto.

Examples of compound (VI) include phenylhydrazine, methylhydrazine, ethylhydrazine, isopropylhydrazine and the like.

The amount of compound (VI) to be used is generally 1 to mol, preferably 2 to 5 mol, per 1 mol of compound (Vb) or compound (V'b) or a mixture thereof (or compound (V) or compound (V') or a mixture thereof).

The reaction is carried out without solvent or in a solvent inert to the reaction. The solvent is not particularly limited as long as the reaction proceeds. Preferable examples thereof include alcohols (e.g., methanol, ethanol, 1-propanol, 2-propanol, tert-butyl alcohol, 2-methoxyethanol and the like), organic acids (e.g., formic acid, acetic acid, propionic acid, trifluoroacetic acid, methanesulfonic acid and the like), water and mixed solvents thereof.

The amount of the solvent to be used is generally 1 to 100-fold weights, preferably 10 to 80-fold weights, relative to compound (Vb) or compound (V'b) or a mixture thereof (or compound (V) or compound (V') or a mixture thereof).

The reaction is generally carried out under ice-cooling, at room temperature or under heating with reflux, preferably at 0° C. to 80° C., more preferably 0° C. to 40° C., still more preferably 0° C. to 30° C., particularly preferably at room temperature (about 25° C. (particularly 25±5° C.)).

While the reaction time varies depending on the kind of compound (Vb) or compound (V'b) (or compound (V) or compound (V')), compound (VI) and the solvent, and the reaction temperature, it is generally 0.1 to 10 hr, preferably 0.5 to 5 hr.

Compound (I), compound (I'), compound (II), compound (III), compound (IIIa), compound (IIIb), compound (IV), compound (IV'), compound (Vb), compound (V'b), compound (V), compound (V') and compound (VI) may be in the form of a salt, preferably a pharmacologically acceptable salt. Examples of the salt include salts with inorganic base, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt and the like; aluminum salt; ammonium salt and the like.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrogen chloride, hydrogen bromide, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Compound (II) which is a starting material can be produced according to a method known per se, for example, the method described in non-Patent Document 5.

Among compound (II), compound (IIa):

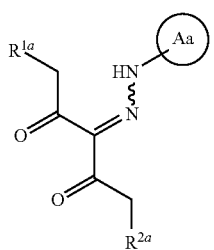

(IIa)

wherein each symbol is as defined above,
is a novel compound. 1-Methoxy-3-(2-phenylhydrazinylidene)pentane-2,4-dione and 1-phenoxy-3-(2-phenylhydrazinylidene)pentane-2,4-dione and a compound wherein $R^{1a}$ is an ethenyloxy group or a benzyloxy group are not encompassed in compound (IIa).

Preferable embodiments of $R^{1a}$, $R^{2a}$ and Ring Aa of compound (IIa) include those exemplified as preferable embodiments for $R^1$, $R^2$ and Ring A of compound (II). Among compound (IIa), the compound represented by the formula:

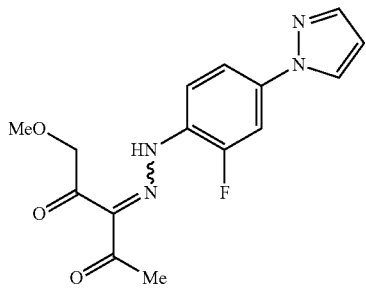 [SMILES: COCC(=O)C(=NNc1ccc(-n2cccn2)cc1F)C(C)=O]

i.e., (3-{2-[2-fluoro-4-(1H-pyrazol-1-yl)phenyl]hydrazinylidene}-1-methoxypentane-2,4-dione) or a salt thereof is preferable.

Compound (IIa) can be produced, for example, according to the following method.

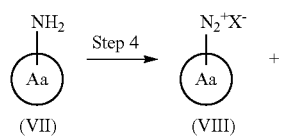

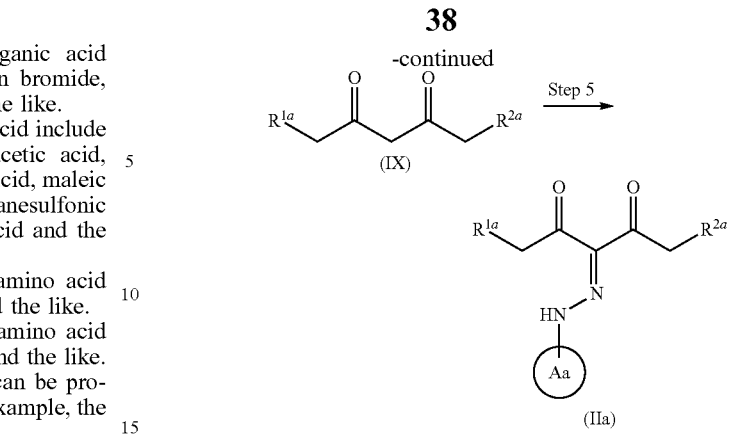

wherein X⁻ is an anion, and examples thereof include anions of halogen atoms (e.g., a fluorine atom, a chlorine atom, a bromine atom, an iodine atom), tetrahalogenoborates (e.g., tetrafluoroborate) and hexahalogenophosphates (e.g., hexafluorophosphate), and the other symbols are as defined above.

Step 4

In this step, compound (VIII) is produced by reacting compound (VII) with a diazotizing agent.

Examples of the diazotizing agent include alkali metal nitrites such as sodium nitrite, potassium nitrite and the like; $C_{2-6}$ alkyl nitrites such as t-butyl nitrite, isoamyl nitrite and the like; nitrosyl chloride, nitrosylsulfuric acid, nitric monoxide and the like. Among them, sodium nitrite is preferable from the aspect of low cost and availability, and an alkyl nitrite is preferable from the aspect of reactivity. Since an alkali metal nitrite is solid at an ambient temperature, it may be used after dissolved in water.

The amount of the diazotizing agent to be used is generally 1 to 5 mol, preferably 1 to 2 mol, per 1 mol of compound (VII), from the aspect of reactivity and economic efficiency.

The reaction is carried out in the presence of an acid, if desired.

Examples of the acid include hydrochloric acid, sulfuric acid, acetic acid and the like, and it may be used in a mixture thereof.

The amount of the acid to be used is generally 1 to 100 mol, preferably 1 to 50 mol, per 1 mol of compound (VII).

The reaction is advantageously carried out without solvent or in a solvent inert to the reaction. The solvent is not particularly limited as long as the reaction proceeds. Preferable examples thereof include water.

The reaction is generally carried out at room temperature or low temperature, preferably −30° C. to 10° C., more preferably 0° C. to 10° C.

While the reaction time varies depending on the kind of compound (VII), the diazotizing agent and the solvent, and the reaction temperature, it is generally 1 min to 3 hr, preferably 1 min to 1 hr.

Step 5

In this step, compound (IIa) is produced by reacting compound (VIII) with compound (IX).

The reaction can be carried out according to the method described in Tetrahedron Lett., 2008, 49(14), 2262-2264 or a method analogous thereto, where desired in the presence of a base.

The amount of compound (IX) to be used is generally 1 to mol, preferably 1 to 2 mol, per 1 mol of compound (VIII).

Examples of the base include sodium acetate.

The amount of the base to be used is generally 1 to 10 equivalents, preferably 2 to 6 equivalents, per 1 mol of compound (VIII).

The reaction is carried out without solvent or in a solvent inert to the reaction. The solvent is not particularly limited as long as the reaction proceeds. Preferable examples thereof include mixed solvents of alcohols (e.g., methanol, ethanol, 1-propanol, 2-propanol, tert-butyl alcohol, 2-methoxyethanol and the like) and water.

The reaction is generally carried out at room temperature or low temperature while cooling in an ice bath.

While the reaction time varies depending on the kind of compound (VIII), compound (IX) and the solvent, and the reaction temperature, it is generally 5 sec to 24 hr, preferably 5 sec to 1 hr.

In the production method of the present invention, the reaction proceeds in high yield by appropriately selecting the reaction temperature in Step 1 and Step 2, and compound (I) can be easily obtained at a low cost by appropriately selecting the reaction temperature in Step 3. Particularly, in the present invention production method, when compound (I) is 1-[2-fluoro-4-(1H-pyrazol-1-yl)phenyl]-5-methoxy-3-(1-phenyl-1H-pyrazol-5-yl)pyridazin-4(1H)-one (compound A), the reaction is carried out generally at 0 to 150° C., preferably 0 to 80° C., further more preferably 0 to 70° C., still more preferably 0 to 65° C. in Step 1 and Step 2.

Compound (IIa) may be in the form of a salt, preferably a pharmacologically acceptable salt, and examples thereof include those similar to the salt exemplified for compound (I) and the like.

Compound (I), compound (I'), compound (II), compound (IIa), compound (III), compound (IIIa), compound (IIIb), compound (IV), compound (IV'), compound (Vb), compound (V'b), compound (V), compound (V') and compound (VI) may be in the form of a hydrate or non-hydrate, and they are each encompassed in compound (I), compound (I'), compound (II), compound (IIa), compound (III), compound (IIIa), compound (IIIb), compound (IV), compound (IV'), compound (Vb), compound (V'b), compound (V), compound (V') and compound (VI).

Since compound (I) or compound (I') or a mixture thereof produced in the production method of the present invention (hereinafter to be collectively referred to as compound (I)) has a superior PDE10A inhibitory activity, it is useful for the prophylaxis or treatment of, for example, the following diseases and symptoms in mammals (e.g., humans, cows, horses, dogs, cats, monkeys, mice, rats and the like, particularly humans).

psychotic disorder (e.g., brief psychotic disorder, shared psychotic disorder);
psychosis induced by alcohol, amphetamine, cannabis, cocaine, hallucinogens, obesity, inhalants, opioids, or phencyclidine; delusional disorder;
anxiety disorder;
movement disorder;
mood disorder;
major depressive disorder;
a major depressive disorder superimposed on a psychotic disorder comprising a delusional disorder or schizophrenia;
major depressive episode of the mild, moderate or severe type;
manic or mixed mood episode;
hypomanic mood episode;
depressive episode with atypical features;
depressive episode with melancholic features;
depressive episode with catatonic features;
mood episode with postpartum onset;
post-stroke depression;
dysthymic disorder;
minor depressive disorder;
autism;
drug addiction;
neurodegenerative disorder;
neurodegeneration associated with cerebral trauma;
neurodegeneration associated with stroke;
neurodegeneration associated with cerebral infarct;
hypoglycemia-induced neurodegeneration;
neurodegeneration associated with epileptic seizure;
neurodegeneration associated with neurotoxin poisoning;
multi-system atrophy;
Alzheimer's disease;
dementia;
multi-infarct dementia;
alcoholic dementia or other drug-related dementia;
dementia associated with intracranial tumors or cerebral trauma;
dementia associated with Huntington's disease or Parkinson's disease;
AIDS-related dementia;
Frontotemporal dementia;
delirium;
amnestic disorder;
post-traumatic stress disorder;
mental retardation;
learning disorder (e.g., reading disorder, mathematics disorder, or a disorder of written expression);
attention-deficit/hyperactivity disorder;
age-related cognitive decline;
premenstrual dysphoric disorder;
post-psychotic depressive disorder of schizophrenia;
bipolar disorder comprising bipolar I disorder, bipolar II disorder;
cyclothymic disorder;
Parkinson's disease;
Huntington's disease;
paranoid;
schizophrenia (e.g., paranoid schizophrenia, disorganized schizophrenia, disorganized schizophrenia, catatonic schizophrenia, undifferentiated schizophrenia, residual schizophrenia);
schizophreniform disorder;
schizoaffective disorder of the delusional type or the depressive type;
personality disorder of the paranoid type;
personality disorder of the schizoid type;
obesity;
metabolic syndrome;
non-insulin dependent diabetes (NIDDM);
glucose intolerance;
pulmonary arterial hypertension (PAH);
Tourette syndrome (TS).

Among them, compound (I) is useful for the prophylaxis or treatment of schizophrenia.

Since compound (I) is superior in metabolic stability, it can be expected to have an excellent therapeutic effect on the above-mentioned diseases even in a low dose.

Compound (I) shows low toxicity, and can be administered safely, as it is, or in a dosage form which is manufactured according to a per se known method for manufacturing pharmaceutical formulations (e.g., methods described in Japanese Pharmacopoeia) such as tablet (including sugar-coated tablet, film-coated tablet, sublingual tablet, orally disintegrating tablet and buccal), pill, powder, granule, capsule (including soft capsule, microcapsule), troche, syrup, liquid, emulsion, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal, and directly to lesion).

Here, as a pharmacologically acceptable carrier, common organic or inorganic carrier substances are used as formulation raw materials. Carriers are added as vehicles, lubricants, binders, disintegrants and the like in the solid formulations; and as solubilizing agents, suspending agents, isotonization agents, buffers, soothing agents and the like in the liquid formulations. If desired, formulation additives such as antiseptics, antioxidants, colorants, sweeteners and the like can be used.

Preferable examples of the excipient include lactose, sucrose, D-mannitol, D-sorbitol, starch, α-starch, dextrin, crystalline cellulose, low-substituted hydroxypropyl cellulose, sodium carboxymethyl cellulose, gum Arabic, pullulan, light silicic anhydride, synthetic aluminum silicate and magnesium metasilicic aluminate.

Preferable examples of the lubricant include magnesium stearate, calcium stearate, talc and colloidal silica.

Preferable examples of the binder include α-starch, sucrose, gelatin, gum Arabic, methyl cellulose, carboxymethyl cellulose, sodium carboxymethyl cellulose, crystalline cellulose, sucrose, D-mannitol, trehalose, dextrin, pullulan, hydroxypropyl cellulose, hydroxypropyl methyl cellulose and polyvinylpyrrolidone.

Preferable examples of the disintegrant include lactose, sucrose, starch, carboxymethyl cellulose, calcium carboxymethyl cellulose, sodium croscarmellose, sodium carboxymethyl starch, light silicic anhydride and low-substituted hydroxypropyl cellulose.

Preferable examples of the solvent include water for injection, physiological saline, Linger solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, tris-aminomethane, cholesterol, triethanolamine, sodium carbonate, sodium citrate, sodium salicylate and sodium acetate.

Preferable examples of the suspending agent include surfactants such as stearyl triethanolamine, sodium lauryl sulfate, laurylamino propionic acid, lecithin, benzalkonium chloride, benzethonium chloride and glycerin monostearate; hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose; polysorbates, and polyoxyethylene-hardened castor oil.

Preferable examples of the isotonization agent include sodium chloride, glycerin, D-mannitol, D-sorbitol and glucose.

Preferable examples of the buffer include buffer solution of phosphates, acetates, carbonates and citrates.

Preferable examples of the soothing agent include benzyl alcohol.

Preferable examples of antiseptic include para-oxybenzoic acid esters, chlorobutanol, benzyl alcohol, phenethyl alcohol, dehydroacetic acid and sorbic acid.

Preferable examples of antioxidant include sulfites and ascorbates.

Preferable examples of the colorant include water soluble edible tar dyes (e.g., edible dyes such as Food Red No. 2 and No. 3, Food Yellow No. 4 and No. 5, Food Blue No. 1 and 2), water insoluble lake dyes (e.g., aluminum salts of the above-mentioned water soluble edible tar dyes) and natural dyes (e.g., β-carotene, chlorophyll, red iron oxide).

Preferable examples of the sweetener include sodium saccharin, dipotassium glycyrrhizate, aspartame and stevia.

While the content of compound (I) in the pharmaceutical composition of the present invention varies depending on the dosage form, dose of compound (I), and the like, it is, for example, about 0.1 to 100 wt %, preferably about 0.1-95 wt %, relative to the entire amount of the composition.

While the dose of compound (I) varies depending on the subject of administration, administration route, target disease, symptom and the like, for example, for oral administration to a schizophrenia patient (adult, about 60 kg weight), it is generally about 0.1 to about 20 mg/kg body weight, preferably about 0.2 to about 10 mg/kg body weight, more preferably about 0.5 to about 10 mg/kg body weight as a single dose, which is desirably administered once to several times (e.g., 3 times) a day.

Compound (I) can be administered as a single active substance, or can be administered in combination with other medicaments such as other drugs used in the treatment of psychosis, specially schizophrenia and bipolar disorder, obsessive-compulsive disorder, major depression, Parkinson's disease, Alzheimer's disease, cognitive impairment and/or memory loss, for example, nicotinic α7 agonists, nicotinic α7 partial agonists, nicotinic α7 positive allosteric modulators, PDE2 inhibitors, PDE4 inhibitors, PDE5 inhibitors, other PDE inhibitors, calcium channel blockers, muscarinic m1 and m2 modulators, adenosine receptor modulators, ampakines, glycine transporter 1 inhibitors, NMDA-R modulators, mGluR modulators, dopamine modulators, serotonin modulators, selective serotonin reuptake inhibitors, serotonin and norepinephrine reuptake inhibitors, norepinephrine and dopamine reuptake inhibitors, triple reuptake inhibitors, cannabinoid modulators and cholinesterase inhibitors (e.g., donepezil, rivastigimine and galantamine). In such combinations, each active ingredient can be administered either in accordance with their usual dosage range or a dose below their usual dosage range, and can be administered either simultaneously or sequentially.

Examples of the drug suitable for combination with compound (I) (hereinafter to be referred to as concomitant drug) include other suitable schizophrenia drugs including, but not limited to, Haldol, Clozaril, Zyprexa, Risperdal, Abilify, Geodon, Invega and Seroquel; bipolar disorder drugs including, but not limited to, Lithium, Zyprexa, Abilify and Depakote; Parkinson's disease drugs including, but not limited to, Levodopa, Parlodel, Permax, Mirapex, Tasmar, Kemadrin, Artane and Cogentin; agents used in the treatment of major depression including, but not limited to, Elavil, Tofranil, Norpramin, Pamelor, Paxil, Prozac, Zoloft, Wellbutrin, Lexapro, Remeron, Effexor and Cymbalta; agents used in the treatment of Alzheimer's disease including, but not limited to, Reminyl, Cognex, Aricept, Exelon, Akatinol, Neotropin, Eldepryl, Estrogen and Cliquinol; agents used in the treatment of dementia including, but not limited to, Mellaril, Haldol, Risperdal, Cognex, Aricept and Exelon; agents used in the treatment of epilepsy including, but not limited to, Dilantin, Luminal, Tegretol, Depakote, Depakene, Zarontin, Neurontin, Barbita, Solfeton and Felbatol; agents used in the treatment of multiple sclerosis including, but not limited to, Detrol, Ditropan XL, OxyContin, Betaseron, Avonex, Azathioprine, Trexall and Copaxone; agents used in the treatment of Huntington's disease including, but not limited to, Elavil, Tofranil, Norpramin, Pamelor, Paxil, Prozac, Zoloft, Nitoman, Haldol, Thorazine, Mellaril, Dogmatil, Seroquel, Clozaril and Risperdal; agents used in the treatment of diabetes including, but not limited to, PPAR ligands (e.g., agonists, antagonists, such as Rosiglitazone, Troglitazone and Pioglitazone), insulin secretagogues (e.g., sulfonylurea drugs such as Glyburide, Glimepiride, Chlopropamide, Tolbutamide and Glipizide, and non-sulfonyl secretagogues), α-glucosidase inhibitors (e.g., Acarbose, Miglitol and Voglibose), insulin sensitizers (e.g., the PPAR-γ agonists such as glitazones and biguanides, PTP-1B inhibitors, DPP-IV inhibitors and 11beta-HSD inhibitors), hepatic glucose output lowering compounds (e.g., glucagon antagonists and metformin, such as Glucophage and Glucophage XR), insulin and insulin derivatives (both long and short acting forms and formulations of insulin); and antiobesity drugs, including, but not limited to, β-3 agonists, CB-1 agonists, neuropeptide Y5 inhibitors, Ciliary Neurotrophic Factor and derivatives (e.g., Axokine), appetite suppressants (e.g., Sibutramine) and lipase inhibitors (e.g., Orlistat).

The form of administration of compound (I) with a concomitant drug is not particularly limited and is acceptable as long as compound (I) is combined with a concomitant drug at the time of administration. Examples of such forms of administration are as follows:

(1) Administration of a single formula obtained simultaneous formulation of compound (I) with a concomitant drug,
(2) Simultaneous administration via the same administration route for two kinds of formulas obtained by independent formulations of compound (I) and a concomitant drug,
(3) Administrations at different times via the same administration route for two kinds of formulas obtained by independent formulations of compound (I) and a concomitant drug,
(4) Simultaneous administration via different administration routes for two kinds of formulas obtained by independent formulations of compound (I) and a concomitant drug,
(5) Administrations at different times via different administration routes for two kinds of formulas obtained by independent formulations of compound (I) and a concomitant drug (for example, administration in the order of compound (I) to a concomitant drug, or administration in the reversed order). Hereinafter, these forms of administration are collectively abbreviated as the combination agent of the present invention.

When administering the combination agent of the present invention, a concomitant drug and compound (I) can be administered simultaneously. Alternatively, compound (I) can be administered after a concomitant drug is administered, or a concomitant drug can be administered after compound (I) is administered. When administering at different times, the time difference depends upon the active ingredients to be administered, drug forms and methods of administration. For example, when a concomitant drug is administered first, compound (I) can be administered within 1 min to 3 days, preferably within 10 min to 1 day, more preferably within 15 min to 1 hour after the concomitant drug is administered. When compound (I) is administered first, a concomitant drug can be administered within 1 min to 1 day, preferably within 10 min to 6 hours, more preferably within 15 min to 1 hour after compound (I) is administered.

If there are no problems with side effects of concomitant drugs, any dosages can be set. A daily dosage as a concomitant drug depends upon dosages, administration subjects, administration routes, target diseases, symptoms and the like. For example, for oral administration to a schizophrenia patient (adult, about 60 kg weight), it is generally about 0.1 to 20 mg/kg body weight, preferably about 0.2 to 10 mg/kg body weight, more preferably about 0.5 to 10 mg/kg body weight as a single dose, which is desirably administered once to several times (e.g., 3 times) a day.

If compound (I) is used in combination with a concomitant drug, the respective dosages can be reduced within a safe range with consideration of the opposite effects of the respective drugs.

The combination agent of the present invention shows low toxicity. For example, the compound of (I) or(and) the above-mentioned concomitant drug can be combined with a pharmacologically acceptable carrier according to the known method to prepare a pharmaceutical composition such as tablet (including sugar-coated tablet and film-coated tablet), powder, granule, capsule (including soft capsule), liquid, injection, suppository, sustained-release agent and the like. These compositions can be administered safely orally or parenterally (e.g., including locally, rectally, intravenously etc.).

The pharmacologically acceptable carriers that can be used for manufacturing the combination agent of the present invention can be the same as those used in the pharmaceutical composition comprising compound (I) as mentioned above.

A mixing ratio between compound (I) and a concomitant drug in the combination agent of the present invention can be selected appropriately based on the administration subjects, administration routes and diseases.

The above-mentioned concomitant drugs can be used in a combination of two or more kinds thereof in an appropriate ratio.

A dosage of the concomitant drug can be selected appropriately based on the dosages used clinically. In addition, a mixing ratio between compound (I) and a concomitant drug can be selected appropriately based on the administration subjects, administration routes, target diseases, symptoms, combinations and the like. For example, if the administration subject is human, a concomitant drug can be used in an amount ranging from 0.01 to 100 parts by weight relative to 100 parts by weight of compound (I).

For example, the content of compound (I) in the combination agent of the present invention varies with the drug form of formulation. Generally, it is within the range from about 0.01 to 99.9 wt %, preferably from about 0.1 to 50 wt %, more preferably from about 0.5 to 20 wt %, relative to the entire amount of the formulation.

The content of a concomitant drug in the combination agent of the present invention varies with the drug form of formulation. Generally it is within the range from about 0.01 to 99.9 wt %, preferably from about 0.1 to 50 wt %, more preferably from about 0.5 to 20 wt %, relative to the entire amount of the formulation.

The content of an additive such as carriers in the combination agent of the present invention varies with the drug form of formulation. Generally it is within the range from about 1 to 99.99 wt %, preferably from about 10 to 90 wt %, relative to the entire amount of the formulation.

When compound (I) and a concomitant drug are formulated independently, the same contents can be applied.

Since the dosages may fluctuate under various conditions as mentioned above, a dosage less than the above-mentioned dosages may be sufficient or it may be necessary to administer at a dosage exceeding the range.

EXAMPLES

The present invention is explained in detail in the following by referring to Reference examples and Examples, and which are not to be construed as limitative.

In the Reference examples and Examples, the "room temperature" means about 25° C.

Reference Example 1

1) 1-methoxy-3-(1-phenyl-1H-pyrazol-5-yl)propan-2-ol

To a solution of 1-phenyl-1H-pyrazole (5.0 g) in tetrahydrofuran (150 mL) was added dropwise 1.6M n-butyllithium n-hexane solution (22.8 mL) at −78° C. The mixture was stirred at the same temperature for 1 hr, and 2-(methoxymethyl)oxirane (9.2 g) was added thereto. The mixture was stirred at room temperature for 1 hr, 1M hydrochloric acid was added thereto, and the mixture was concentrated under reduced pressure to evaporate tetrahydrofuran. The residue was extracted with ethyl acetate, and the extract was purified by silica gel column chromatography to give 1-methoxy-3-(1-phenyl-1H-pyrazol-5-yl)propan-2-ol (2.44 g, 30%).

2) 1-methoxy-3-(1-phenyl-1H-pyrazol-5-yl)propan-2-one

To a solution of dimethylsulfoxide (505 mg) in tetrahydrofuran (3 mL) was added trifluoroacetic anhydride (407 mg) at −50° C., and the mixture was stirred for 15 min. A solution of 1-methoxy-3-(1-phenyl-1H-pyrazol-5-yl)propan-2-ol (300 mg) in tetrahydrofuran (2 mL) was added thereto at the same temperature. The mixture was stirred at 0° C. for 15 min, triethylamine (523 mg) was added thereto, and the mixture was stirred for 1 hr. The mixture was stirred at room temperature for additional 3 hr, and extracted with ethyl acetate and 10% sodium carbonate aqueous solution. The organic layer was washed successively with 1M hydrochloric acid and 10% brine, and concentrated under reduced pressure. The residue was purified by silica gel column chromatography to give 1-methoxy-3-(1-phenyl-1H-pyrazol-5-yl)propan-2-one (183 mg, 62%).

3) 1-{2-[2-fluoro-4-(1H-pyrazol-1-yl)phenyl]hydrazinylidene}-3-methoxy-1-(1-phenyl-1H-pyrazol-5-yl)propan-2-one To 3M hydrochloric acid (1.1 mL) was added 2-fluoro-4-(1H-pyrazol-1-yl)aniline hydrochloride (139 mg). A mixture of sodium nitrite (67 mg) and water (0.2 mL) was added dropwise thereto at 0° C., and the mixture was stirred at the same temperature for 2 hr. This solution was added dropwise to a solution of 1-methoxy-3-(1-phenyl-1H-pyrazol-5-yl)propan-2-one (150 mg) and sodium acetate (321 mg) in methanol (1.4 mL) at 0° C., and the mixture was stirred at the same temperature for 1 hr. The mixture was extracted with water and ethyl acetate, and the organic layer was concentrated under reduced pressure. The residue was purified by silica gel column chromatography to give 1-{2-[2-fluoro-4-(1H-pyrazol-1-yl)phenyl]hydrazinylidene}-3-methoxy-1-(1-phenyl-1H-pyrazol-5-yl)propan-2-one (110 mg, 40%).

4) 1-[2-fluoro-4-(1H-pyrazol-1-yl)phenyl]-5-methoxy-3-(1-phenyl-1H-pyrazol-5-yl)pyridazin-4(1H)-one To a solution of 1-{2-[2-fluoro-4-(1H-pyrazol-1-yl)phenyl]hydrazinylidene}-3-methoxy-1-(1-phenyl-1H-pyrazol-5-yl)propan-2-one (100 mg) in N,N-dimethylacetamide (1 mL) was added N,N-dimethylformamide dimethyl acetal (43 mg), and the mixture was stirred at 80° C. for 2 hr. Then, water (1.5 mL) was added thereto at room temperature, the mixture was stirred overnight, and the crystals were collected by filtration. The wet crystals were dried to give 1-[2-fluoro-4-(1H-pyrazol-1-yl)phenyl]-5-methoxy-3-(1-phenyl-1H-pyrazol-5-yl)pyridazin-4(1H)-one (50 mg, 49%).

Reference Example 2

1) 2-fluoro-4-(1H-pyrazol-1-yl)aniline

A mixture of 2-fluoro-4-iodoaniline (1000 g), 1H-pyrazole (345 g), cesium carbonate (2887 g) and 1,2-dimethoxyethane (5 L) was degassed. To the reaction mixture were added copper(I) iodide (24.1 g) and trans-1,2-cyclohexanediamine (48.2 g) with stirring, and the mixture was stirred under nitrogen atmosphere at room temperature for 20 min, and then stirred with heating at the internal temperature of 85° C. to 86° C. for 72 hr. The reaction mixture was diluted with water (7.5 L), and extracted with ethyl acetate (10 L). The aqueous layer was extracted with ethyl acetate (10 L). The organic layers was combined, washed with saturated brine (0.10 L), dried over magnesium sulfate, and concentrated. The residue was purified by silica gel column chromatography (ethyl acetate/hexane) to give the title compound (650 g) as pale yellow crystals.

2) methyl 2-{2-[2-fluoro-4-(1H-pyrazol-1-yl)phenyl]hydrazinylidene}-4-methoxy-3-oxobutanoate To a mixture of 2-fluoro-4-(1H-pyrazol-1-yl)aniline (271 g) and 6N hydrochloric acid (1.53 L) was added dropwise a solution of sodium nitrite (158 g)/water (380 mL) over 30 min at the internal temperature of 5° C. to 15° C., and the mixture was stirred at the same temperature for 90 min. To a suspension of methyl 4-methoxy-3-oxobutanoate (223 g), sodium acetate (753 g) and methanol (3 L) was added dropwise the above-mentioned solution over 30 min at the internal temperature of 5° C. to 21° C., and the mixture was stirred at the same temperature for 20 min. To the reaction mixture was added dropwise water (3 L) over 30 min at the same temperature, and the mixture was stirred at the same temperature for 90 min. The resulting crystals were collected by filtration, and washed with water (3 L). A solution of ethanol (3.38 L)/diisopropyl ether (2.25 L) was added thereto, and the mixture was stirred at room temperature for 30 min. The crystals were collected by filtration, washed successively with diisopropyl ether (1 L) and hexane (1 L), and dried to give the title compound (472 g) as orange crystals.

3) methyl 1-[2-fluoro-4-(1H-pyrazol-1-yl)phenyl]-5-methoxy-4-oxo-1,4-dihydropyridazine-3-carboxylate A mixture of methyl 2-{2-[2-fluoro-4-(1H-pyrazol-1-yl)phenyl]hydrazinylidene}-4-methoxy-3-oxobutanoate (945 g), N,N-dimethylformamide dimethyl acetal (4.5 L) and N,N-dimethylformamide (0.45 L) was stirred at the internal temperature of 85° C. for 60 min. The reaction mixture was cooled to 5° C. over 1 hr, and stirred at the same temperature for 30 min. The resulting crystals were collected by filtration, washed with a solution of ethyl acetate (1.4 L)/hexane (2.8 L), and dried to give the title compound (920 g) as pale yellow crystals.

4) 1-[2-fluoro-4-(1H-pyrazol-1-yl)phenyl]-5-methoxy-4-oxo-1,4-dihydropyridazine-3-carboxylic acid To a mixture of methyl 1-[2-fluoro-4-(1H-pyrazol-1-yl)phenyl]-5-methoxy-4-oxo-1,4-dihydropyridazine-3-carboxylate (280 g) and methanol (5 L) was added dropwise 1N aqueous sodium hydroxide solution (1.63 L) over 30 min at the internal temperature of 5° C. to 10° C., and the mixture was stirred at room temperature for 1 hr. To the reaction mixture was added dropwise 1N hydrochloric acid (1.63 L) over 30 min at the internal temperature of 5° C. to 10° C., and the mixture was stirred at the same temperature for 30 min. The crystals were collected by filtration, washed successively with water (0.75 L) and a solution of ethanol (0.84 L)/diisopropyl ether (0.56 L), and dried to give the title compound (242 g) as pale yellow crystals.

5) 1-[2-fluoro-4-(1H-pyrazol-1-yl)phenyl]-N,5-dimethoxy-N-methyl-4-oxo-1,4-dihydropyridazine-3-carboxamide To a mixture of 1-[2-fluoro-4-(1H-pyrazol-1-yl)phenyl]-5-methoxy-4-oxo-1,4-dihydropyridazine-3-carboxylic acid (148.8 g) and N,N-dimethylformamide (576 mL) were added N,O-dimethylhydroxylamine hydrochloride (48.3 g), 1-hydroxybenzotriazole monohydrate (76 g), 1-ethyl-3-(3-dimethylaminopropyl)-carbodiimide hydrochloride (95 g) and triethylamine (132 mL), and the mixture was stirred at 25° C. for 3 hr. To the reaction mixture were added N,O-dimethylhydroxylamine hydrochloride (8.80 g), 1-hydroxybenzotriazole (13.8 g), 1-ethyl-3-(3-dimethylaminopropyl)-carbodiimide hydrochloride (17.3 g) and triethylamine (25.1 mL), and the mixture was stirred at 25° C. for 3 hr. To the reaction mixture were added N,O-dimethylhydroxylamine hydrochloride (8.80 g), 1-hydroxybenzotriazole (13.8 g), 1-ethyl-3-(3-dimethylaminopropyl)-carbodiimide hydrochloride (17.3 g) and triethylamine (25.1 mL), and the mixture was stirred overnight at 30° C. To the reaction mixture was added water (3.5 L), and the mixture was stirred at 0° C. for 4 hr. The resulting crystals were collected by filtration, and washed with water (1 L). A solution of ethanol (600 mL)/diisopropyl ether (400 mL) was added thereto, and the mixture was stirred. The crystals were collected by filtration, and washed successively with diisopropyl ether (200 mL) and hexane (200 mL) to give the title compound (138.7 g).

6) 3-acetyl-1-[2-fluoro-4-(1H-pyrazol-1-yl)phenyl]-5-methoxypyridazin-4(1H)-one

To 1-[2-fluoro-4-(1H-pyrazol-1-yl)phenyl]-N,5-dimethoxy-N-methyl-4-oxo-1,4-dihydropyridazine-3-carboxamide (20 g) was added tetrahydrofuran (1.6 L), and the mixture was heated at 60° C. to dissolve the compound, and allowed to be cooled. 1M methylmagnesium bromide tetrahydrofuran solution (200 mL) was cooled to −78° C., the above-mentioned solution was added dropwise thereto at the internal temperature of −78° C. to −50° C., and the reaction mixture was stirred at −78° C. for 2 hr. To the reaction mixture was added saturated aqueous ammonium chloride solution (200 mL), and the mixture was allowed to be warmed to room temperature. The organic layer was washed with saturated brine (300 mL×3), and the aqueous layers were combined, and extracted with ethyl acetate (500 mL). The organic layers were combined, and concentrated. The aqueous layer was removed by decantation from the brownish-red residue, tetrahydrofuran (30 mL) was added thereto, and the mixture was purified by silica gel column chromatography (methanol/ethyl acetate). To the resulting crystals was added ethyl acetate (25 mL), and the mixture was stirred, and diisopropyl ether (75 mL) was added thereto. The crystals were collected by filtration, and washed with a solution of ethyl acetate (12.5 mL)/diisopropyl ether (37.5 mL) to give the title compound (13.9 g).

7) 3-[3-(dimethylamino)prop-2-enoyl]-1-[2-fluoro-4-(1H-pyrazol-1-yl)phenyl]-5-methoxypyridazin-4(1H)-one To a mixture of 3-acetyl-1-[2-fluoro-4-(1H-pyrazol-1-yl)phenyl]-5-methoxypyridazin-4(1H)-one (700 g) and acetonitrile (3.5 L) was added N,N-dimethylacetamide dimethyl acetal (3.5 L) at the internal temperature of 15° C. to 20° C. The reaction mixture was stirred with heating at the internal temperature of 82° C. for 4 hr, and ice-cooled for 1 hr. The resulting crystals were collected by filtration, washed successively with acetonitrile (3 L) and diisopropyl ether (3 L), and dried under reduced pressure at 50° C. for 6 hr to give the title compound (725.3 g) as brown crystals.

8) 1-[2-fluoro-4-(1H-pyrazol-1-yl)phenyl]-5-methoxy-3-(1-phenyl-1H-pyrazol-5-yl)pyridazin-4(1H)-one To a mixture of 3-[3-(dimethylamino)prop-2-enoyl]-1-[2-fluoro-4-(1H-pyrazol-1-yl)phenyl]-5-methoxypyridazin-4(1H)-one (774.8 g) and ethanol (3.9 L) was added dropwise a solution of phenylhydrazine (210.8 mL) in 10% trifluoroacetic acid/ethanol (7.75 L) over 1 hr at the internal temperature of 0 to 5° C., and the mixture was stirred at the internal temperature of 20° C. to 25° C. for 3 days. The reaction mixture was ice-cooled for 1 hr, and the resulting crystals were collected by filtration, washed with ethanol (3.9 L), and dried under reduced pressure at 60° C. for 6 hr to give crude crystals (826.0 g) of 1-[2-fluoro-4-(1H-pyrazol-1-yl)phenyl]-5-methoxy-3-(1-phenyl-H-pyrazol-5-yl)pyridazin-4(1H)-one as yellow crystals.

To the crude 1-[2-fluoro-4-(1H-pyrazol-1-yl)phenyl]-5-methoxy-3-(1-phenyl-1H-pyrazol-5-yl)pyridazin-4(1H)-one (1.75 kg) was added dimethylsulfoxide (14.9 L), and the mixture was heated at 70° C. to dissolve the compound. The solution was filtered, and the reaction container and filter were washed with dimethylsulfoxide (0.88 L). To the filtrate was added dropwise ethanol (15.0 L) over 1.5 hr at 60° C., and the mixture was cooled to 4° C. over 2 hr, and stirred at 2° C. to 4° C. for 40 min. The resulting crystals were collected by filtration, washed with ethanol (14 L), dried overnight in air, and then dried under reduced pressure at 60° C. for 4 hr to give the recrystallized (once) product (1.48 kg) of 1-[2-fluoro-4-(1H-pyrazol-1-yl)phenyl]-5-methoxy-3-(1-phenyl-1H-pyrazol-5-yl)pyridazin-4(1H)-one.

To the above-mentioned recrystallized (once) product (1.48 kg) of 1-[2-fluoro-4-(1H-pyrazol-1-yl)phenyl]-5-methoxy-3-(1-phenyl-1H-pyrazol-5-yl)pyridazin-4(1H)-one was added dimethylsulfoxide (10.7 L), and the mixture was heated at 75° C. to dissolve the compound. To the solution was added dropwise ethanol (13.1 L) over 1 hr at 65° C. to 70° C., and the mixture was cooled to 5° C. over 1.5 hr, and stirred at the internal temperature of 2° C. to 5° C. for 45 min. The resulting crystals were collected by filtration, washed with ethanol (11.8 L), dried overnight in air, and then dried under reduced pressure at 50° C. for 2 hr to give the recrystallized (twice) product (1.40 kg) of 1-[2-fluoro-4-(1H-pyrazol-1-yl)phenyl]-5-methoxy-3-(1-phenyl-1H-pyrazol-5-yl)pyridazin-4(1H)-one.

Reference Example 3

1) 2-fluoro-4-(1H-pyrazol-1-yl)aniline

A mixture of 2-fluoro-4-iodoaniline (1000 g), 1H-pyrazole (345 g), cesium carbonate (2887 g) and 1,2-dimethoxyethane (5 L) was degassed. To the reaction mixture were added copper(I) iodide (24.1 g) and trans-1,2-cyclohexanediamine (48.2 g) with stirring, and the mixture was stirred at room temperature for 20 min under nitrogen atmosphere, and then stirred with heating at the internal temperature of 85° C. to 86° C. for 72 hr. The reaction mixture was diluted with water (7.5 L), and extracted with ethyl acetate (10 L). The aqueous layer was extracted with ethyl acetate (10 L). The organic layers were combined, washed with saturated brine (10 L), dried over magnesium sulfate, and concentrated. The residue was purified by silica gel column chromatography (ethyl acetate/hexane) to give the title compound (650 g) as pale yellow crystals.

2) methyl 2-{2-[2-fluoro-4-(1H-pyrazol-1-yl)phenyl]hydrazinylidene}-4-methoxy-3-oxobutanoate To a mixture of 2-fluoro-4-(1H-pyrazol-1-yl)aniline (271 g) and 6N hydrochloric acid (1.53 L) was added dropwise a solution of sodium nitrite (158 g)/water (380 mL) over 30 min at the internal temperature of 5° C. to 15° C., and the mixture was stirred at the same temperature for 90 min. To a suspension of methyl 4-methoxy-3-oxobutanoate (223 g), sodium acetate (753 g) and methanol (3 L) was added dropwise the above-mentioned solution over 30 min at the internal temperature of 5° C. to 21° C., and the mixture was stirred at the same temperature for 20 min. To the reaction mixture was added dropwise water (3 L) over 30 min at the same temperature, and the mixture was stirred at the same temperature for 90 min. The resulting crystals were collected by filtration, and washed with water (3 L). A solution of ethanol (3.38 L)/diisopropyl ether (2.25 L) was added thereto, and the mixture was stirred at room temperature for 30 min. The crystals were collected by filtration, washed successively with diisopropyl ether (1 L) and hexane (1 L), and dried to give the title compound (472 g) as orange crystals.

3) methyl 1-[2-fluoro-4-(1H-pyrazol-1-yl)phenyl]-5-methoxy-4-oxo-1,4-dihydropyridazine-3-carboxylate A mixture of methyl 2-{2-[2-fluoro-4-(1H-pyrazol-1-yl)phenyl]hydrazinylidene}-4-methoxy-3-oxobutanoate (945 g), N,N-dimethylformamide dimethyl acetal (4.5 L) and N,N-dimethylformamide (0.45 L) was stirred at the internal temperature of 85° C. for 60 min. The reaction mixture was cooled over 1 hr to 5° C., and stirred at the same temperature for 30 min. The resulting crystals were collected by filtration, washed with a solution of ethyl acetate (1.4 L)/hexane (2.8 L), and dried to give the title compound (920 g) as pale yellow crystals.

4) 1-[2-fluoro-4-(1H-pyrazol-1-yl)phenyl]-5-methoxy-4-oxo-1,4-dihydropyridazine-3-carboxylic acid To a mixture of methyl 1-[2-fluoro-4-(1H-pyrazol-1-yl)phenyl]-5-methoxy-4-oxo-1,4-dihydropyridazine-3-carboxylate (280 g) and methanol (5 L) was added dropwise 1N aqueous sodium hydroxide solution (1.63 L) over 30 min at the internal temperature of 5° C. to 10° C., and the mixture was stirred at room temperature for 1 hr. To the reaction mixture was added dropwise 1N hydrochloric acid (1.63 L) over 30 min at the internal temperature of 5° C. to 10° C., and the mixture was stirred at the same temperature for 30 min. The crystals were collected by filtration, washed successively with water (0.75 L) and a solution of ethanol (0.84 L)/diisopropyl ether (0.56 L), and dried to give the title compound (242 g) as pale yellow crystals.

5) 5-({1-[2-fluoro-4-(1H-pyrazol-1-yl)phenyl]-5-methoxy-4-oxo-1,4-dihydropyridazin-3-yl}carbonyl)-2,2-dimethyl-1,3-dioxane-4,6-dione A solution of 1-[2-fluoro-4-(1H-pyrazol-1-yl)phenyl]-5-methoxy-4-oxo-1,4-dihydropyridazine-3-carboxylic acid (625 g), N,N-dimethyl-4-aminopyridine (462 g), 2,2-dimethyl-1,3-dioxane-4,6-dione (273 g) and 1-ethyl-3-(3-dimethylaminopropyl)carbodiimide hydrochloride (363 g) in N,N-dimethylformamide (2.5 L) was stirred at room temperature for 3 days. The reaction mixture was diluted with water (7.5 L), and sodium chloride (900 g) was added thereto. The resulting solid was collected by filtration, and dried under reduced pressure to give the title compound (870 g) as a white solid.

6) 3-acetyl-1-[2-fluoro-4-(1H-pyrazol-1-yl)phenyl]-5-methoxypyridazin-4(1H)-one

A mixture of 5-({1-[2-fluoro-4-(1H-pyrazol-1-yl)phenyl]-5-methoxy-4-oxo-1,4-dihydropyridazin-3-yl}carbonyl)-2,2-dimethyl-1,3-dioxane-4,6-dione (300 g) and acetic acid (1500 mL) was heated with reflux for 2 hr. The reaction mixture was concentrated under reduced pressure, the residue was diluted with tetrahydrofuran, and the insoluble substance was removed by filtration. The filtrate was purified by silica gel column chromatography (tetrahydrofuran) to give the title compound (76 g) as a pale yellow solid.

7) 3-[3-(dimethylamino)prop-2-enoyl]-1-[2-fluoro-4-(1H-pyrazol-1-yl)phenyl]-5-methoxypyridazin-4(1H)-one To a mixture of 3-acetyl-1-[2-fluoro-4-(1H-pyrazol-1-yl)phenyl]-5-methoxypyridazin-4(1H)-one (700 g) and acetonitrile (3.5 L) was added N,N-dimethylacetamide dimethyl acetal (3.5 L) at the internal temperature of 15° C. to 20° C. The reaction mixture was stirred with heating at the internal temperature of 82° C. for 4 hr, and ice-cooled for 1 hr. The resulting crystals were collected by filtration, washed successively with acetonitrile (3 L) and IPE (3 L), and dried under reduced pressure at 50° C. for 6 hr to give the title compound (725.3 g) as brown crystals.

8) 1-[2-fluoro-4-(1H-pyrazol-1-yl)phenyl]-5-methoxy-3-(1-phenyl-1H-pyrazol-5-yl)pyridazin-4(1)-one To a mixture of 3-[3-(dimethylamino)prop-2-enoyl]-1-[2-fluoro-4-(1H-pyrazol-1-yl)phenyl]-5-methoxypyridazin-4(1H)-one (774.8 g) and ethanol (3.9 L) was added dropwise a solution of phenylhydrazine (210.8 mL) in 10% trifluoroacetic acid/ethanol (7.75 L) over 1 hr at the internal temperature of 0 to 5° C., and the mixture was stirred at the internal temperature of 20° C. to 25° C. for 3 days. The reaction mixture was ice-cooled for 1 hr, and the resulting crystals were collected by filtration, washed with ethanol (3.9 L), and dried under reduced pressure at 60° C. for 6 hr to give crude crystals (826.0 g) of 1-[2-fluoro-4-(1H-pyrazol-1-yl)phenyl]-5-methoxy-3-(1-phenyl-1H-pyrazol-5-yl)pyridazin-4(1H)-one as yellow crystals.

To the crude 1-[2-fluoro-4-(1H-pyrazol-1-yl)phenyl]-5-methoxy-3-(1-phenyl-1H-pyrazol-5-yl)pyridazin-4(1H)-one (1.75 kg) was added dimethylsulfoxide (14.9 L), and the mixture was heated at 70° C. to dissolve the compound. The solution was filtered, and the reaction container and filter were washed with dimethylsulfoxide (0.88 L). To the filtrate was added dropwise ethanol (15.0 L) over 1.5 hr at 60° C., and the mixture was cooled to 4° C. over 2 hr, and stirred at 2° C. to 4° C. for 40 min. The resulting crystals were collected by filtration, washed with ethanol (14 L), dried overnight in air, and then dried under reduced pressure at 60° C. for 4 hr to give the recrystallized (once) product (1.48 kg) of 1-[2-fluoro-4-(1H-pyrazol-1-yl)phenyl]-5-methoxy-3-(1-phenyl-1H-pyrazol-5-yl)pyridazin-4(1H)-one.

To the above-mentioned recrystallized (once) product (1.48 kg) of 1-[2-fluoro-4-(1H-pyrazol-1-yl)phenyl]-5-methoxy-3-(1-phenyl-1H-pyrazol-5-yl)pyridazin-4(1H)-one was added dimethylsulfoxide (10.7 L), and the mixture was heated at 750° C. to dissolve the compound. To the solution was added dropwise ethanol (13.1 L) over 1 hr at 65° C. to 70° C., and the mixture was cooled to 5° C. over 1.5 hr, and stirred at the internal temperature of 2° C. to 5° C. for 45 min. The resulting crystals were collected by filtration, washed with ethanol (11.8 L), dried overnight in air, and then dried under reduced pressure at 50° C. for 2 hr to give the recrystallized (twice) product (1.40 kg) of 1-[2-fluoro-4-(1H-pyrazol-1-yl)phenyl]-5-methoxy-3-(1-phenyl-1H-pyrazol-5-yl)pyridazin-4(1H)-one.

Example 1

3-[3-(dimethylamino)-2-methylprop-2-enoyl]-1-[2-fluoro-4-(1H-pyrazol-1-yl)phenyl]-5-methoxypyridazin-4(1H)-one To a solution of 3-{2-[2-fluoro-4-(1H-pyrazol-1-yl)phenyl]hydrazinylidene}-1-methoxyhexane-2,4-dione (300 mg) in N,N-dimethylacetamide (3 mL) was added N,N-dimethylformamide dimethyl acetal (323 mg) at room temperature, and the mixture was stirred at 80° C. for 1 hr. The mixture was extracted with ethyl acetate and saturated brine at room temperature. The organic layer was concentrated under reduced pressure, and the residue was purified by silica gel column chromatography (ethyl acetate) to give 3-[3-(dimethylamino)-2-methylprop-2-enoyl]-1-[2-fluoro-4-(1H-pyrazol-1-yl)phenyl]-5-methoxypyridazin-4(1H)-one (218 mg, 62%).

$^1$H NMR (500 MHz, DMSO-$d_6$) δ1.96 (3H, s), 3.08 (3H, brs), 3.79 (3H, s), 6.60-6.68 (1H, m), 6.96 (1H, brs), 7.74-8.10 (4H, m), 8.44-8.51 (1H, m), 8.63-8.70 (1H, m).

Example 2

3-[3-(dimethylamino)prop-2-enoyl]-1-[2-fluoro-4-(1H-pyrazol-1-yl)phenyl]-5-phenoxypyridazin-4(1H)-one To a solution of 3-{2-[2-fluoro-4-(1H-pyrazol-1-yl)phenyl]hydrazinylidene}-1-phenoxypentane-2,4-dione (300 mg) in DMAc (3 mL) was added N,N-dimethylformamide dimethyl acetal (282 mg) at room temperature, and the mixture was stirred at 80° C. for 1 hr. The mixture was extracted with ethyl acetate and saturated brine at room temperature. The organic layer was concentrated under reduced pressure, and the residue was purified by silica gel column chromatography (ethyl acetate) to give 3-[3-(dimethylamino)prop-2-enoyl]-1-[2-fluoro-4-(1H-pyrazol-1-yl)phenyl]-5-phenoxypyridazin-4(1H)-one (323 mg, 92%).

$^1$H NMR (500 MHz, DMSO-$d_6$) δ2.83 (3H, s), 3.12 (3H, brs), 5.19 (1H, brs), 6.60-6.69 (1H, m), 6.98-7.21 (3H, m), 7.29-7.39 (2H, m), 7.49 (1H, brs), 7.79-7.97 (3H, m), 8.01-8.08 (1H, m), 8.66 (1H, d, J=2.2 Hz), 8.92 (1H, brs).

Example 3

1) 2-fluoro-4-(1H-pyrazol-1-yl)aniline hydrochloride

To dimethylsulfoxide (1400 mL) were added 2-fluoro-4-iodoaniline (200 g), pyrazole (86.2 g) and tripotassium phosphate (215.0 g). Copper(I) oxide (14.5 g) was added thereto, and then DMSO (200 mL) was added thereto. The mixture was stirred at 100° C. for 5 hr. After the completion of the reaction, water (2000 mL), ethyl acetate (2400 mL) and 10% (w/w) aqueous citric acid solution (2000 mL) were added thereto at 45° C., and the mixture was stirred at the same temperature for 30 min, and separated at room temperature. The organic layer was washed successively with a mixture of 12% (w/w) aqueous ammonia (1000 mL) and 20% (w/w) aqueous ammonium chloride solution (1000 mL), a mixture of 6% (w/w) aqueous ammonia (1000 mL) and 20% (w/w) aqueous ammonium chloride solution (1000 mL), 10% (w/w) aqueous ammonium chloride solution (2000 mL), and water (2000 mL). To the organic layer was added dropwise 4M hydrogen chloride-ethyl acetate solution (173 mL) at room temperature, and the mixture was stirred. The crystals were collected by filtration, and washed with ethyl acetate (800 mL). The wet crystals were dried to give 2-fluoro-4-(1H-pyrazol-1-yl)aniline hydrochloride (130.7 g, 73%).

$^1$H NMR (500 MHz, DMSO-$d_6$) δ6.49-6.51 (1H, m), 7.05-7.20 (1H, m), 7.42-7.57 (1H, m), 7.60-7.71 (2H, m), 8.38 (1H, d, J=2.5 Hz).

2) 3-{2-[2-fluoro-4-(1H-pyrazol-1-yl)phenyl]hydrazinylidene}-1-methoxypentane-2,4-dione t-BuONa (33.2 g) was added to toluene (240 mL) at room temperature. A solution of methyl methoxyacetate (30.0 g) in acetone (16.7 g) was added thereto at 0-10° C., and the mixture was stirred at room temperature for 18 hr. The pH of the mixture was adjusted to 10.5 with 2M hydrochloric acid (120 mL) and 2M aqueous sodium hydroxide solution (80 mL) at 0-10° C. After separation, to the aqueous layer were successively added acetic acid (24.2 g), methanol (611 mL) and sodium acetate (61.8 g) (Solution (1)).

In another container, to 3M hydrochloric acid (256 mL) was added 2-fluoro-4-(1H-pyrazol-1-yl)aniline hydrochloride (32.2 g). A mixture of sodium nitrite (13.4 g) and water (32 mL) was added dropwise thereto at 0-10° C., and the mixture was stirred at the same temperature for 1 hr (Solution (2)). To Solution (1) was added dropwise Solution (2) at 0-10° C., and the mixture was stirred at the same temperature for 2 hr. The crystals were collected by filtration, and washed successively with water (640 mL) and 50% (v/v) aqueous methanol solution (64 mL). The wet crystals were dried to give 3-{2-[2-fluoro-4-(1H-pyrazol-1-yl)phenyl]hydrazinylidene}-1-methoxypentane-2,4-dione (45.0 g, 94%).

$^1$H NMR (500 MHz, DMSO-$d_6$) δ2.42 (3H, brs), 3.32 (3H, s), 4.56 (3H, brs), 6.55-6.65 (1H, m), 7.72-8.05 (4H, m), 8.56 (1H, s), 14.49 (1H, brs).

3) 3-[3-(dimethylamino)prop-2-enoyl]-1-[2-fluoro-4-(1H-pyrazol-1-yl)phenyl]-5-methoxypyridazin-4(H)-one To a solution of N,N-dimethylformamide dimethyl acetal (5.6 g) in N,N-dimethylacetamide (13.5 mL) was added 3-{2-[2-fluoro-4-(1H-pyrazol-1-yl)phenyl]hydrazinylidene}-1-methoxypentane-2,4-dione (5 g) at room temperature, and the container used for the compound was washed with N,N-dimethylacetamide (1.5 mL). The mixture was stirred at 62° C. for 3 hr. Ethyl acetate (75 mL) was added thereto at 50° C., and the mixture was stirred at room temperature for 2 hr. The crystals were collected by filtration, and washed with ethyl acetate (15 mL). The wet crystals were dried to give 3-[3-(dimethylamino)prop-2-enoyl]-1-[2-fluoro-4-(1H-pyrazol-1-yl)phenyl]-5-methoxypyridazin-4(1H)-one (40.1 g, 83%).

$^1$H NMR (500 MHz, DMSO-$d_6$) δ2.82 (3H, s), 3.09 (3H, brs), 3.79 (3H, s), 5.24 (1H, brs), 6.60-6.67 (1H, m), 7.45 (1H, brs), 7.79-8.08 (4H, m), 8.46-8.52 (1H, m), 8.63-8.70 (1H, m).

4) 1-[2-fluoro-4-(1H-pyrazol-1-yl)phenyl]-5-methoxy-3-(1-phenyl-1H-pyrazol-5-yl)pyridazin-4(1H)-one To a solution of 3-[3-(dimethylamino)prop-2-enoyl]-1-[2-fluoro-4-(1H-pyrazol-1-yl)phenyl]-5-methoxypyridazin-4(1H)-one (3 g) in acetic acid (22.5 mL) was added phenylhydrazine (889 mg) at room temperature, and the mixture was stirred for 3 hr. 1M Hydrochloric acid (22.5 mL) was added dropwise thereto at room temperature, and the mixture was stirred for 1 hr. The crystals were collected by filtration, and washed successively with a mixture of acetic acid (2.1 mL) and ethanol (3.9 mL), and ethanol (15 mL). The wet crystals were dried to give 1-[2-fluoro-4-(1H-pyrazol-1-yl)phenyl]-5-methoxy-3-(1-phenyl-1H-pyrazol-5-yl)pyridazin-4(1H)-one (3.0 g, 89%).

Example 4

1) 1-phenylpentane-2,4-dione

To a suspension of t-BuOK (4.48 g) in THF (25 mL) was added dropwise a solution of methyl phenylacetate (5.00 g) and acetone (2.13 g) in THF (5 mL) at 0-10° C., and the mixture was stirred overnight at room temperature. The reaction mixture was poured into 2M hydrochloric acid (20 mL), and the mixture was extracted with ethyl acetate (20 mL). The organic layer was washed with saturated brine (10 mL), and concentrated under reduced pressure. The residue was purified by silica gel column chromatography to give 1-phenylpentane-2,4-dione (1.12 g, 19.1%).

$^1$H NMR (500 MHz, CDCl$_3$) δ2.02 (3H, s), 3.58 (2H, s), 5.43 (1H, s), 7.22-7.40 (5H, m).

2) 3-{2-[2-fluoro-4-(1H-pyrazol-1-yl)phenyl]hydrazinylidene}-1-phenylpentane-2,4-dione To a mixture of 2-fluoro-4-(1H-pyrazol-1-yl)aniline hydrochloride (1.10 g) and 3 M hydrochloric acid (8.8 mL) was added dropwise a mixture of sodium nitrite (534 mg) and water (1.1 mL) at 0-10° C., and the mixture was stirred at the same temperature for 1 hr. The obtained reaction mixture was added dropwise to a mixture of 1-phenylpentane-2,4-dione (1.00 g) and sodium acetate (2.54 g) in methanol (11 mL) at 0-10° C. The mixture was stirred at room temperature for 1 hr, and the crystals were collected by filtration, and washed successively with water (10 mL) and 50% aqueous methanol (5 mL). The wet crystals were dried to give crude 3-{2-[2-fluoro-4-(1H-pyrazol-1-yl)phenyl]hydrazinylidene}-1-phenylpentane-2,4-dione. The crude 3-{2-[2-fluoro-4-(1H-pyrazol-1-yl)phenyl]hydrazinylidene}-1-phenylpentane-2,4-dione (1.26 g) was suspended in ethanol (12.6 mL), and the suspension was stirred at 50° C. for 1.5 hr. The mixture was allowed to be cooled to room temperature, and the crystals were collected by filtration, and washed with ethanol (12.6 mL). The wet crystals were dried to give 3-{2-[2-fluoro-4-(1H-pyrazol-1-yl)phenyl]hydrazinylidene}-1-phenylpentane-2,4-dione (1.05 g, 80.6%).

$^1$H NMR (500 MHz, CDCl$_3$) δ2.60 (3H, s), 4.25 (3H, s), 6.45-6.54 (1H, m), 7.23-7.36 (5H, m), 7.56-7.64 (2H, m), 7.71-7.76 (1H, m), 7.81-7.88 (1H, m), 7.90-7.94 (1H, m), 14.84 (1H, brs).

3) 3-[3-(dimethylamino)prop-2-enoyl]-1-[2-fluoro-4-(1H-pyrazol-1-yl)phenyl]-5-phenylpyridazin-4(1H)-one A mixture of 3-{2-[2-fluoro-4-(1H-pyrazol-1-yl)phenyl]hydrazinylidene}-1-phenylpentane-2,4-dione (100 mg) and dimethylformamide dimethyl acetal (2 mL) was stirred at 80° C. for 5 hr. The reaction mixture was concentrated under reduced pressure, and the residue was purified by silica gel column chromatography to give 3-[3-(dimethylamino)prop-2-enoyl]-1-[2-fluoro-4-(1H-pyrazol-1-yl)phenyl]-5-phenylpyridazin-4(1H)-one (111 mg, 93.7%).

$^1$H NMR (500 MHz, CDCl$_3$) δ2.90 (3H, brs), 3.14 (3H, brs), 5.73 (1H, brs), 6.61-6.67 (1H, m), 7.36-7.49 (3H, m), 7.56-7.64 (1H, m), 7.67-7.85 (5H, m), 7.97 (1H, d, J=2.5 Hz), 8.25 (1H, d, J=2.5 Hz).

Example 5

1) tert-butyl 2-acetyl-3-oxo-4-(phenylsulfanyl)butanoate

To a suspension of t-BuONa (4.32 g) in THF (35 mL) was added dropwise tert-butyl 3-oxobutanoate (7.12 g) at 0-10° C., and the mixture was stirred at room temperature for 1.5 hr. (Phenylsulfanyl)acetyl chloride (7.00 g) was added dropwise thereto at 0-10° C., and the mixture was stirred overnight at room temperature. To the reaction mixture was added 2M hydrochloric acid (70 mL), and the mixture was extracted with ethyl acetate (70 mL). The organic layer was washed with saturated brine (18 mL), and concentrated under reduced pressure. The residue was purified by silica gel column chromatography, and then purified by suspension with ethyl acetate/hexane=1/1 (21 mL) to give tert-butyl 2-acetyl-3-oxo-4-(phenylsulfanyl)butanoate (3.90 g, 33.7%).

$^1$H NMR (500 MHz, CDCl$_3$) δ1.56 (9H, s), 2.36 (3H, s), 4.05 (2H, s), 7.20-7.32 (3H, m), 7.38-7.43 (2H, m).

2) 1-(phenylsulfanyl)pentane-2,4-dione tert-Butyl 2-acetyl-3-oxo-4-(phenylsulfanyl)butanoate (3.80 g) was dissolved in trifluoroacetic acid (11 mL), and the solution was stirred overnight at room temperature. To the reaction mixture was added water (38 mL), and the mixture was extracted with ethyl acetate (57 mL). The organic layer was washed successively with water (19 mL) and saturated brine (19 mL), and concentrated under reduced pressure, and the residue was passed through a small amount of silica gel to give crude 1-(phenylsulfanyl)pentane-2,4-dione. This was used for the next step.

$^1$H NMR (500 MHz, CDCl$_3$) δ2.04 (3H, s), 3.61 (2H, s), 5.71 (1H, s), 7.14-7.43 (5H, m).

3) 3-{2-[2-fluoro-4-(1H-pyrazol-1-yl)phenyl]hydrazinylidene}-1-(phenylsulfanyl)pentane-2,4-dione To a mixture of 2-fluoro-4-(1H-pyrazol-1-yl)aniline hydrochloride (1.85 g) and 3 M hydrochloric acid (15 mL) was added dropwise a mixture of sodium nitrite (778 mg) and water (1.9 mL) at 0-10° C., and the mixture was stirred at the same temperature for 1 hr. The obtained reaction mixture was added dropwise to a mixture of the crude 1-(phenylsulfanyl)pentane-2,4-dione (2.71 g), sodium acetate (3.56 g) and water (15 mL) in methanol (28 mL) at 0-10° C. The mixture was stirred at room temperature for 1 hr, and the crystals were collected by filtration, and washed successively with water (19 mL) and 50% aqueous methanol (19 mL). The wet crystals were dried to give crude 3-{2-[2-fluoro-4-(1H-pyrazol-1-yl)phenyl]hydrazinylidene}-1-(phenylsulfanyl)pentane-2,4-dione. The crude 3-{2-[2-fluoro-4-(1H-pyrazol-1-yl)phenyl]hydrazinylidene}-1-(phenylsulfanyl)pentane-2,4-dione (500 mg) was suspended in a mixture of ethyl acetate (1 mL) and heptane (2 mL). After stirring at room temperature for 1 hr, the crystals were collected by filtration, and washed with a mixture of ethyl acetate (1 mL) and heptane (2 mL). The wet crystals were dried to give 3-{2-[2-fluoro-4-(1H-pyrazol-1-yl)phenyl]hydrazinylidene}-1-(phenylsulfanyl)pentane-2,4-dione (391 mg, 86.9%).

$^1$H NMR (500 MHz, CDCl$_3$) δ2.58 (3H, s), 4.22 (3H, s), 6.46-6.54 (1H, m), 7.15-7.24 (1H, m), 7.24-7.32 (2H, m), 7.39-7.47 (2H, m), 7.50-7.56 (1H, m), 7.57-7.66 (1H, m), 7.67-7.77 (2H, m), 7.86-7.96 (1H, m), 14.84 (1H, brs).

4) 3-[3-(dimethylamino)prop-2-enoyl]-1-[2-fluoro-4-(1H-pyrazol-1-yl)phenyl]-5-(phenylsulfanyl)pyridazin-4 (H)-one A mixture of 3-{2-[2-fluoro-4-(1H-pyrazol-1-yl)phenyl]hydrazinylidene}-1-(phenylsulfanyl)pentane-2,4-dione (100 mg) and dimethylformamide dimethyl acetal (0.7 mL) was concentrated under reduced pressure, to the residue was added ethyl acetate (10 mL), and the mixture was stirred at room temperature for 1 hr. The crystals were collected by filtration, and washed with ethyl acetate. The wet crystals were dried to give 3-[3-(dimethylamino)prop-2-enoyl]1-[2-fluoro-4-(1H-pyrazol-1-yl)phenyl]-5-(phenylsulfanyl)pyridazin-4(1H)-one (110 mg, 77.4%).

$^1$H NMR (500 MHz, DMSO-d$_6$) δ2.84 (3H, brs), 3.12 (3H, brs), 5.23 (1H, brs), 6.59-6.67 (1H, m), 7.30-7.48 (5H, m), 7.76-7.87 (2H, m), 7.87-7.94 (1H, m), 7.95-8.05 (1H, m), 8.43 (1H, brs), 8.59-8.67 (1H, m).

Formulation Example 1

A plain tablet (core tablet) containing compound A was produced as follows at the composition ratio shown below. That is, compound A (17.660 g, the content was amended), D-mannitol (4257.0 g, the weight was amended), crystalline cellulose (369.4 g) and sodium starch glycolate (263.9 g) were placed in a fluidized bed dryer granulator (FD-5S, manufactured by POWREX CORPORATION), and the mixture was preheated and mixed. The mixture was granulated while spraying an aqueous solution (2638.0 g) of hydroxypropyl cellulose (158.3 g) in purified water (2480.0 g) to give granulated powders. The obtained granulated powders (4651.0 g) were passed through a powermill (P-3S, manufactured by Showa Kagaku Kikai Kosakusho) to give sized powders. The sized powders (4435.0 g), crystalline cellulose (138.6 g) and magnesium stearate (46.217 g) were placed in a tumbler mixer (TM-15, manufactured by Showa Kagaku Kikai Kosakusho), and mixed to give mixed powders. The mixed powders were tableted by a rotary tableting machine (AQUA0512SS2AI, manufactured by Kikusui Seisakusho, Ltd.) using a 9 mmφ punch to give plain tablets (core tablets, 300 mg per tablet).

<Composition of Plain Tablet (Core Tablet) Containing Compound A>

| | |
|---|---|
| compound A | 1 mg |
| D-mannitol | 242 mg |
| crystalline cellulose | 30 mg |
| hydroxypropyl cellulose | 9 mg |
| sodium starch glycolate | 15 mg |
| magnesium stearate | 3 mg |
| total | 300 mg |

The obtained plain tablets (core tablet, 2991.0 g) were placed in a film coating machine (DRC-500, manufactured by POWREX CORPORATION), and a film coating solution (1448.0 g) having the composition ratio shown below was sprayed thereto to give rapid disintegrating tablets (about 312.2 mg per tablet).

<Composition of Coating Solution>

| | |
|---|---|
| Hypromellose | 9 mg |
| macrogol 6000 | 2 mg |
| titanium oxide | 1 mg |
| iron sesquioxide | 0.067 mg |
| yellow iron sesquioxide | 0.133 mg |
| purified water | 109.8 mg |
| total (solid content) | 122 (12.2) mg |

Formulation Example 2

A plain tablet (core tablet) containing compound A was produced as follows at the composition ratio shown below. That is, compound A (176.6 g, the content was amended), D-mannitol (4098.0 g, the weight was amended), crystalline cellulose (369.4 g) and sodium starch glycolate (263.9 g)

were placed in a fluidized bed dryer granulator (FD-5S, manufactured by POWREX CORPORATION), and the mixture was preheated and mixed. The mixture was granulated while spraying an aqueous solution (2638.0 g) of hydroxypropyl cellulose (158.3 g) in purified water (2480.0 g) to give granulated powders. The obtained granulated powders (4651.0 g) were passed through a powermill (P-3S, manufactured by Showa Kagaku Kikai Kosakusho) to give sized powders. The sized powders (4435.0 g), crystalline cellulose (138.6 g) and magnesium stearate (46.212 g) were placed in a tumbler mixer (TM-15, manufactured by Showa Kagaku Kikai Kosakusho), and mixed to give mixed powders. The mixed powders were tableted by a rotary tableting machine (AQUA0512SS2AI, manufactured by Kikusui Seisakusho, Ltd.) using a 9 mmϕ punch to give plain tablets (core tablets, 300 mg per tablet).

<Composition of Plain Tablet (Core Tablet) Containing Compound A>

| | |
|---|---|
| compound A | 10 mg |
| D-mannitol | 233 mg |
| crystalline cellulose | 30 mg |
| hydroxypropyl cellulose | 9 mg |
| sodium starch glycolate | 15 mg |
| magnesium stearate | 3 mg |
| total | 300 mg |

The obtained plain tablets (core tablet, 2991.0 g) were placed in a film coating machine (DRC-500, manufactured by POWREX CORPORATION), and a film coating solution (1369.0 g) having the composition ratio shown in Formulation Example 1 was sprayed thereto to give rapid disintegrating tablets (about 312.2 mg per tablet).

Formulation Example 3

A plain tablet (core tablet) containing compound A was produced as follows at the composition ratio shown below. That is, compound A (1766.0 g, the content was amended), D-mannitol (2508.0 g, the weight was amended), crystalline cellulose (369.4 g) and sodium starch glycolate (263.9 g) were placed in a fluidized bed dryer granulator (FD-5S, manufactured by POWREX CORPORATION), and the mixture was preheated and mixed. The mixture was granulated while spraying an aqueous solution (2638.0 g) of hydroxypropyl cellulose (158.3 g) in purified water (2480.0 g) to give granulated powders. The obtained granulated powders (4651.0 g) were passed through a powermill (P-3S, manufactured by Showa Kagaku Kikai Kosakusho) to give sized powders. The sized powders (4435.0 g), crystalline cellulose (138.6 g) and magnesium stearate (46.207 g) were placed in a tumbler mixer (TM-15, manufactured by Showa Kagaku Kikai Kosakusho), and mixed to give mixed powders. The mixed powders were tableted by a rotary tableting machine (AQUA0512SS2AI, manufactured by Kikusui Seisakusho, Ltd.) using a 9 mm punch to give plain tablets (core tablets, 300 mg per tablet).

<Composition of Plain Tablet (Core Tablet) Containing Compound A>

| | |
|---|---|
| compound A | 100 mg |
| D-mannitol | 143 mg |
| crystalline cellulose | 30 mg |
| hydroxypropyl cellulose | 9 mg |
| sodium starch glycolate | 15 mg |
| magnesium stearate | 3 mg |
| total | 300 mg |

The obtained plain tablets (core tablet, 2991.0 g) were placed in a film coating machine (DRC-500, manufactured by POWREX CORPORATION), and a film coating solution (1458.0 g) having the composition ratio shown in Formulation Example 1 was sprayed thereto to give rapid disintegrating tablets (about 312.2 mg per tablet).

INDUSTRIAL APPLICABILITY

According to the present invention, from compound (II) as a starting material, which is an unsymmetric diketone, pyridazinone compound (I) or (I') can be easily produced in high yield, at a low cost, in a suitable method for industrial production, with regioselectivity due to the structure of the substituent.

This application is based on patent application No. 032326/2013 filed in Japan, the contents of which are hereby incorporated by reference.

The invention claimed is:

1. A method of producing a compound represented by the formula (I) or formula (I'):

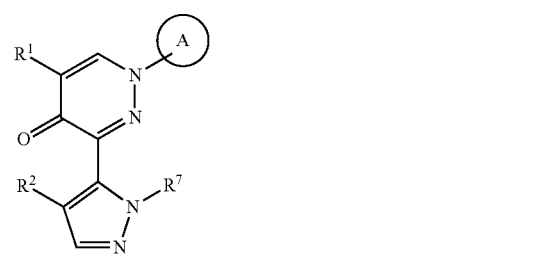

(I)

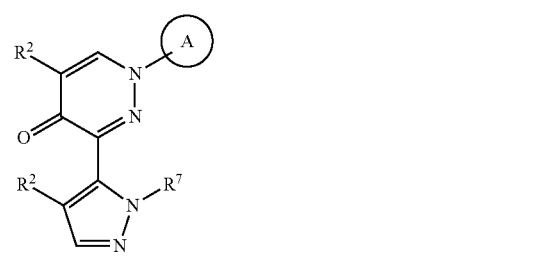

(I')

wherein
R$^1$ is
(i) a C$_{6-14}$ aryl group,
(ii) —OR$^8$ wherein R$^8$ is a C$_{1-10}$ alkyl group or a C$_{6-14}$ aryl group, or
(iii) —SR$^8$ wherein R$^8$ is a C$_{6-14}$ aryl group,
R$^2$ is a hydrogen atom or a C$_{1-6}$ alkyl group,
Ring A is benzene substituted by 5- or 6-membered monocyclic aromatic heterocyclic group(s), and optionally further optionally substituted by 1 to 5 halogen atoms, and
R$^7$ is phenyl,
or a mixture thereof or a salt thereof, which comprises step (1): a step of reacting a compound represented by the formula (II):

(II)

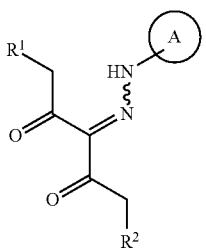

wherein each symbol is as defined above,
or a salt thereof, with a compound represented by the formula (IIIa):

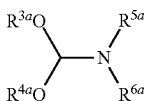
(IIIa)

wherein
$R^{3a}$, $R^{4a}$, $R^{5a}$ and $R^{6a}$ are each independently a $C_{1-6}$ alkyl group,
or a salt thereof, to give a compound represented by the formula (IV) or formula (IV'):

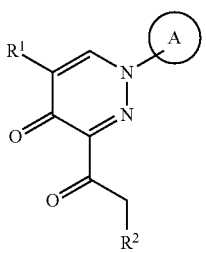
(IV)

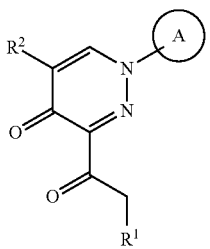
(IV')

wherein each symbol is as defined above,
or a mixture thereof or a salt thereof;
step (2): a step of reacting the compound represented by the formula (IV) or formula (IV') or a mixture thereof or a salt thereof with a compound represented by the formula (IIIb):

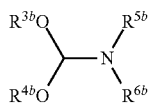
(IIIb)

wherein
$R^{3b}$, $R^{4b}$, $R^{5b}$ and $R^{6b}$ are each independently a $C_{1-6}$ alkyl group,
or a salt thereof, to give a compound represented by the formula (Vb) or formula (V'b):

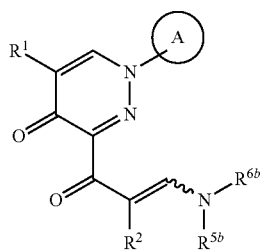
(Vb)

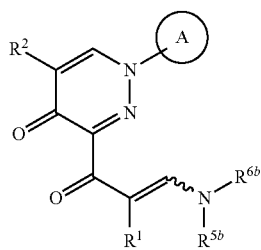
(V'b)

wherein each symbol is as defined above,
or a mixture thereof or a salt thereof; and
step (3): a step of reacting the compound represented by formula (Vb) or formula (V'b) or a mixture thereof or a salt thereof, with a compound represented by the formula (VI):

$R^7NH$—$NH_2$ (VI)

wherein each symbol is as defined above,
or a salt thereof.

2. The method of claim 1, wherein the compound represented by the obtained formula (IV) or formula (IV') or a mixture thereof or a salt thereof obtained in step (1) is subjected to step (2) without isolation.

3. The method of claim 1, wherein $R^1$ is methoxy, and $R^2$ is a hydrogen atom.

4. The method of claim 1, wherein Ring A is 4-(pyrazol-1-yl)-2-fluorobenzene, and $R^7$ is phenyl.

5. The method of claim 1, wherein $R^1$ is methoxy, $R^2$ is a hydrogen atom, Ring A is 4-(pyrazol-1-yl)-2-fluorobenzene, and $R^7$ is phenyl.

* * * * *